(12) United States Patent
Cai et al.

(10) Patent No.: US 12,389,931 B2
(45) Date of Patent: Aug. 19, 2025

(54) OYSTER PEPTIDE WITH EFFECT OF IMPROVING SEXUAL FUNCTION AND PREPARATION METHOD THEREOF

(71) Applicant: CHINA NATIONAL RESEARCH INSTITUTE OF FOOD & FERMENTATION INDUSTRIES CO., LTD., Beijing (CN)

(72) Inventors: Muyi Cai, Beijing (CN); Ruizeng Gu, Beijing (CN); Haixin Zhang, Beijing (CN); Wenying Liu, Beijing (CN); Ying Wei, Beijing (CN); Lei Fang, Beijing (CN); Xingchang Pan, Beijing (CN); Zhe Dong, Beijing (CN); Lu Lu, Beijing (CN); Ming Zhou, Beijing (CN); Yuchen Wang, Beijing (CN); Kong Ling, Beijing (CN); Yuan Bi, Beijing (CN)

(73) Assignee: CHINA NATIONAL RESEARCH INSTITUTE OF FOOD & FERMENTATION INDUSTRIES CO., LTD., Beijing (CN)

(*) Notice: Subject to any disclaimer, the term of this patent is extended or adjusted under 35 U.S.C. 154(b) by 569 days.

(21) Appl. No.: 17/728,905

(22) Filed: Apr. 25, 2022

(65) Prior Publication Data
US 2022/0248737 A1    Aug. 11, 2022

Related U.S. Application Data

(63) Continuation of application No. PCT/CN2020/076909, filed on Feb. 27, 2020.

(30) Foreign Application Priority Data

Oct. 29, 2019 (CN) .................. 201911039453.4

(51) Int. Cl.
A23L 33/18    (2016.01)
A23J 1/04    (2006.01)
(Continued)

(52) U.S. Cl.
CPC .................. *A23L 33/18* (2016.08); *A23J 1/04* (2013.01); *A23J 3/04* (2013.01); *A23J 3/341* (2013.01);
(Continued)

(58) Field of Classification Search
CPC ... A23L 33/18; A23L 5/23; A23L 5/25; A23L 5/273; A23L 17/65; A23L 33/17;
(Continued)

(56) References Cited

FOREIGN PATENT DOCUMENTS

| CN | 103805663 A | 5/2014 |
|---|---|---|
| CN | 104798980 A | 7/2015 |

(Continued)

OTHER PUBLICATIONS

Hong et al., Comparison of Taste Components between Triploid and Diploid Oyster, 2002, Journal of Ocean University of Oingdao, vol. 1, No. I, pp. 55-58 (Year: 2002).*
(Continued)

*Primary Examiner* — Robert B Mondesi
*Assistant Examiner* — Naghmeh Nina Moazzami
(74) *Attorney, Agent, or Firm* — J.C. Patents

(57) ABSTRACT

An oyster peptide with an effect of improving sexual function and a preparation method thereof are provided, the oyster peptide at least includes peptide segments RI, IR and VR in its composition. Based on a mass of the oyster peptide, a content of the RI is ≥3.60 mg/100 g, a content of the IR is ≥7.60 mg/100 g, and a content of the VR is ≥6.50 mg/100 g.

7 Claims, 17 Drawing Sheets

(51) Int. Cl.
*A23J 3/04* (2006.01)
*A23J 3/34* (2006.01)
*A23L 5/20* (2016.01)
*A23L 17/00* (2016.01)
*A61P 15/10* (2006.01)
*B01D 15/18* (2006.01)
*B01D 15/32* (2006.01)
*B01D 15/36* (2006.01)
*B01D 21/26* (2006.01)
*B01D 71/02* (2006.01)
*C07K 1/18* (2006.01)
*C07K 1/20* (2006.01)
*C07K 1/36* (2006.01)
*C07K 14/435* (2006.01)

(52) U.S. Cl.
CPC ................................. *A23L 5/23* (2016.08);
*A23L 5/25* (2016.08); *A23L 5/273* (2016.08);
*A23L 17/65* (2016.08); *A61P 15/10* (2018.01);
*B01D 15/1871* (2013.01); *B01D 15/327*
(2013.01); *B01D 15/362* (2013.01); *B01D*
*21/262* (2013.01); *B01D 71/02* (2013.01);
*C07K 1/18* (2013.01); *C07K 1/20* (2013.01);
*C07K 1/36* (2013.01); *C07K 14/43504*
(2013.01); *A23V 2002/00* (2013.01)

(58) Field of Classification Search
CPC ...... A23J 1/04; A23J 3/04; A23J 3/341; A61P
15/10; B01D 15/1871; B01D 15/327;
B01D 15/362; B01D 21/262; B01D
71/02; B01D 61/147; B01D 71/024;
C07K 1/18; C07K 1/20; C07K 1/36;
C07K 14/43504; A23V 2002/00
See application file for complete search history.

(56) References Cited

FOREIGN PATENT DOCUMENTS

| | | |
|---|---|---|
| CN | 105219826 A | 1/2016 |
| CN | 107815482 A | 3/2018 |
| CN | 108085355 A | 5/2018 |
| CN | 109007848 A | 12/2018 |
| JP | H06239897 A | 8/1994 |

OTHER PUBLICATIONS

Lodeiros et al., Tropical and Subtropical Ostreidae of The American Pacific: Taxonomy, Biology, Ecology, and Genetics, 2020, Journal of Shellfish Research, vol. 39, No. 2, 181-206 (Year: 2020).*
English translation of CN109845995A. (Year: 2019).*
English translation of CN103636914A. (Year: 2014).*
English translation of CN102488074A. (Year: 2013).*
International Search Report of PCT/CN2020/076909.
Notice of Allowance of the priority application CN 201911039453. 4.

* cited by examiner

OYSTER PEPTIDE WITH EFFECT OF IMPROVING SEXUAL FUNCTION AND PREPARATION METHOD THEREOF

CROSS-REFERENCE TO RELATED APPLICATIONS

This application is a continuation of International Application No. PCT/CN2020/076909, filed on Feb. 27, 2020, which claims priority to Chinese Patent Application No. 201911039453.4, filed on Oct. 29, 2019. Both of the above applications are hereby incorporated by reference in their entireties.

TECHNICAL FIELD

The present disclosure relates to an oyster peptide with effect of improving sexual function and a preparation method thereof, which belong to the field of biotechnology.

BACKGROUND

Oysters, also known as fresh oysters, grow in temperate and tropical oceans and belong to bivalve mollusks of Ostreidae. With tender meat, delicious flavor and unique taste, oysters have gradually become people's favorite table delicacies.

Studies have shown that, besides better taste, oysters also have characteristics of high protein content and low fat content, and contain eight types of amino acids required by human body, as well as glycogen, taurine, cystine, vitamin A, vitamin B1, vitamin B2, vitamin D, vitamin E, fucose, copper, zinc, manganese, barium, phosphorus, calcium, magnesium, aluminum and organic materials, etc. Therefore, in recent years, there have been many reports of researches on drugs or health products using oysters as raw materials.

At the present stage, in order to further improve the absorption of nutritional ingredients in oysters by the human body, oysters are often used as raw materials for enzymolysis, so as to separate different small peptides that are beneficial to life activities of the organism or have physiological effects. These small peptides have certain functions of human metabolism and physiological regulation, and can be directly absorbed in the intestine, with an absorption rate being faster than that of direct eating of oysters. Therefore, enzymolysis of oysters to produce oyster peptides is a new direction for deep processing of oyster.

Nowadays, in a process of producing oyster peptides, enzymolysis of oysters is mostly directed to provide the human body with more nutrients for the purpose of resisting fatigue and improving immunity. Consequently, in the enzymolysis process, it is inevitable to lose some peptides with other functions, which narrows the application scope of oysters and affects the further development of deep processing of oysters.

SUMMARY

The present disclosure provides an oyster peptide, the oyster peptide including a certain mass content of specific functional peptide segments of isoleucyl-arginine (Ile-Arg, IR), arginyl-isoleucine (Arg-Ile, RI) and valyl-arginine (Val-Arg, VR), thereby showing good efficacy on promoting the secretion of testosterone and dihydrotestosterone, etc.

The present disclosure further provides a preparation method of the abovementioned oyster peptide. Through controlling enzymolysis, separation, and purification of an oyster meat raw material, the resulting product definitely contains a certain mass content of functional peptide segments such as isoleucyl-arginine (Ile-Arg, IR), arginyl-isoleucine (Arg-Ile, RI) and valyl-arginine (Val-Arg, VR).

The present disclosure further provides a use of the abovementioned oyster peptide in a product for improving sexual function.

The present disclosure provides an oyster peptide, the oyster peptide at least including peptide segments of isoleucyl-arginine (Ile-Arg, IR), arginyl-isoleucine (Arg-Ile, RI) and valyl-arginine (Val-Arg, VR) in its composition.

Specifically, based on a total mass of the oyster peptide (dry basis), a mass content of the RI is ≥3.60 mg/100 g, a mass content of the IR is ≥7.60 mg/100 g, and a mass content of the VR is ≥6.50 mg/100 g.

Besides, the abovementioned oyster peptide also has the characteristics of small average molecular weight and easiness for absorption. Specifically, a mass content of peptides with a molecular weight less than 1000 u in the oyster peptide is ≥90%.

The oyster peptide according to the present disclosure is obtained by the following: taking shelled oyster meat as a raw material, sequentially performing a protein enrichment treatment (an acid treatment for removing fats and polysaccharides), a protein denaturation treatment (an alkali treatment), an enzymolysis treatment (with a neutral protease and a papain) and a separation and purification treatment; where, in the enzymolysis treatment, an enzymolysis time is 3-6 h, and an enzymolysis temperature is determined by optimal activity temperature of a neutral protease and a papain, specifically, the enzymolysis temperature may be 45-55° C.

In a specific preparation, the oyster meat is first subjected to the acid treatment, that is, the components such as fats and polysaccharides in the oyster meat are separated, so as to increase a protein content of an enzymatic substrate, thereby achieving protein enrichment and improving enzymolysis efficiency. Afterwards, the protein denaturation treatment is performed on a product obtained after the protein enrichment, the oyster protein is denatured by alkali at a certain temperature, which would appear at a micro level that the spatial structure of the oyster protein is damaged and thus more enzymolysis sites for the oyster protein are exposed, thereby being further conducive to improvement of the enzymolysis efficiency. After the protein denaturation treatment is completed, a product obtained after such protein denaturation is used as the enzymatic substrate, which is subjected to enzymolysis by the neutral protease and the papain; and, an enzymolysis product is subjected to enzyme deactivation (e.g., heating up to 115-125° C. for 15 s) so as to obtain an enzymolysis solution.

In the enzymolysis treatment, the amount of enzymes needs to be controlled, so as to ensure that the peptide segments RI, IR and VR in the resultant enzymatic product all have a relatively high mass content as much as possible. Based on a mass of the oyster meat raw material, 0.8-1.6 AU (Anson Unit) of neutral protease and 100000-300000 U (Unit) of papain may be used for 1000 g of the oyster meat raw material.

The enzymolysis solution is subjected to a separation and purification treatment, so as to obtain the oyster peptide according to the present disclosure.

The separation and purification treatment on the enzymolysis solution mainly includes centrifugation, filtration and a column chromatography.

Specifically, at first, the enzymolysis solution is centrifuged to collect a centrifugal supernatant; then the centrifugal supernatant is filtered to separate macromolecular substances, for example, a ceramic membrane with a pore size of 50-200 nm may be used; at last, a filtrate obtained after the filtration is subjected to the column chromatography by a cation exchange chromatography column and a hydrophobic chromatography column in sequence, so that the peptide segments RI, IR and VR in the enzymolysis solution are retained. In specific embodiments, the cation exchange chromatography column may use 732 type cation exchange resin as a packing, the packing having a particle size of 0.315-1.25 mm; and the hydrophobic chromatography column may use Octyl sepharose 4FF type hydrophobic medium as a packing, the packing having a particle size of 45-165 μm.

Subsequently, a liquid product collected by the column chromatography is concentrated and dried to obtain the desired oyster peptide, which includes at least peptide segments RI, IR and VR.

Researches indicate: the abovementioned oyster peptide containing peptide segments RI, IR and VR with respective specific mass contents may significantly promote the production of testosterone and dihydrotestosterone, and facilitate improvement of sexual function; additionally, the components of the oyster peptide with a molecular weight less than 1000 u account for a proportion of greater than 90%, therefore, they are completely absorbed by a human intestine, and are easier to function in a human body.

The present disclosure further provides a preparation method of the abovementioned oyster peptide, including the following steps:
1) adding water to an oyster meat raw material to obtain a mixed material liquid, adding concentrated hydrochloric acid to the mixed material liquid and stirring, centrifuging and collecting a precipitate;
2) adding water to the precipitate to obtain a slurry, adding alkali to perform a protein denaturation treatment at 85-90° C., so as to obtain a denatured solution of oyster protein;
3) adding a neutral protease and a papain to the denatured solution of oyster protein, and performing enzymolysis treatment for 3-6 h, so as to obtain an enzymolysis solution after the above enzymes are inactivated; and
4) centrifuging the enzymolysis solution to obtain a centrifugal supernatant, and then performing filtration and a column chromatography treatment on the centrifugal supernatant in sequence, so as to obtain the oyster peptide.

In the present disclosure, there is no limitation on species and source of oysters, and the oyster meat raw material may be either fresh shelled oyster meat, or thawed oyster meat. After washing the oyster meat raw material, the washed oyster meat may be minced by a mincer, so as to make the subsequent protein enrichment treatment and the protein denaturation treatment better.

Furthermore, in step 1), a mass-to-volume ratio of the oyster meat raw material to the water is 1: (5-8), i.e., 1 kg of oyster meat raw material is mixed with 5-8 L of water to prepare a mixed material liquid. Afterwards, with the temperature controlled to be 20-30° C., the concentrated hydrochloric acid is added to the mixed material liquid, followed by stirring for 60-120 min and centrifuging to collect the precipitate (3000-4000 rpm, 10 min). The purpose of the abovementioned operations is to separate components such as the fat and polysaccharide molecules in the oyster meat from the protein, so that such components stay in the centrifugal supernatant and the protein in the oyster meat is enriched in the precipitate, thereby being beneficial for improving the efficiency of subsequent enzymolysis treatment. A concentrated acid treatment is usually used, considering the safety and convenience of operations and products, a concentrated hydrochloric acid may be used. An amount of the concentrated hydrochloric acid is determined by that of the oyster meat raw material; specifically, 3-5 mL of the concentrated hydrochloric acid per kilogram of the oyster meat raw material is added.

After the precipitate in step 1) is collected, water is added to the precipitate, followed by stirring to prepare a slurry. In that case, the amount of water is determined by that of the oyster meat raw material, for one kilogram of the oyster meat raw material, 0.5-1 L of water is added to the precipitate, followed by stirring to prepare the slurry. Through such treatment, the protein-enriched precipitate may be prepared into a slurry with certain fluidity by the addition of an appropriate amount of water, which is beneficial to the subsequent denaturation treatment and enzymolysis. When too little water is added, the fluidity of the slurry is poor, which is not conducive to the function of enzyme preparations and is easy to reduce the enzymolysis efficiency; when too much water is added, the reaction volume is too large, and the load of subsequent processing (such as concentration, etc.) increases, which may also lead to changes in product composition and structure and the processing cost will also increase correspondingly. The water may be pure water, distilled water, deionized water, etc. In the present disclosure, the distilled water may be used to prepare the mixed material liquid and the slurry.

Furthermore, in step 2), the protein denaturation treatment is performed in a high temperature alkaline environment. Alkaline materials may be added to the prepared slurry, generally a strong alkali, commonly sodium hydroxide or potassium hydroxide, and solid alkali may be directly added to the slurry. Specifically, solid sodium hydroxide is added to the slurry, which is then kept at 85-90° C. under continuous stirring for 60-120 min. Where, 0.8-1.0 g of the solid sodium hydroxide per kilogram of the oyster meat raw material is added. Under this condition, a protease naturally existing in oyster raw material may be deactivated, thereby preventing it from affecting the enzymolysis effect of the neutral protease and the papain; at the same time, the spatial structure of the oyster protein may also be destroyed, exposing more enzyme cleavage sites, which are easy to be enzymatically degraded by proteases. Furthermore, the protein in the slurry has a relatively high content, and its proper hydrolysis in an alkaline environment may also facilitate solving problems of poor fluidity of the slurry and viscous solution, which is beneficial to the subsequent enzymolysis.

The inventors have conducted a lot of studies on how to enable the enzymolysis product of the oyster meat to contain the expected mass content of RI, IR and VR peptide segments, and it is demonstrated that the selection of enzyme preparations and corresponding separation processes have a key influence on the results. During the research, the inventors unexpectedly discover that only use of both the neutral protease and the papain for enzymolysis can not only facilitate obtaining RI, IR and VR peptide segments at the same time, but also be conducive to the subsequent separation and purification of RI, IR and VR peptide segments, thereby further ensuring that the mass content of the RI is ≥3.60 mg/100 g, the mass content of the IR is ≥7.60 mg/100 g, and the mass content of the VR is ≥6.50 mg/100 g.

Especially, in the enzymolysis according to the present disclosure, based on the mass of the oyster meat raw material, an amount of the neutral protease is 0.8-1.6 AU/1000 g, and an amount of the papain is 100000-300000 U/1000 g, i.e., 0.8-1.6 AU of the neutral protease and 100000-300000 U of the papain are needed for per kilogram of the oyster meat raw material. The enzymolysis according to the present disclosure is performed at the optimal activity temperature of the neutral protease and the papain, such as 45-55° C., and the enzymolysis time is controlled to be 3-6 h. Too short enzymolysis time (<1 h) is not conducive to protein degradation, while too long enzymolysis time (for example, more than 7 h) may lead to further degradation of a target peptide segment. The abovementioned enzymolysis may also facilitate the formation of components having a smaller molecular weight (for example, peptides with a molecular weight less than 1000 u), thereby facilitating absorption by human body.

After the enzymolysis is completed, a conventional means for enzyme inactivation in the field may be used to deactivate the enzyme, for example, heating up to 115-125° C. and keeping it for about 15 s.

Furthermore, in step 4), a rotating speed of centrifugation may be controlled to be 3000-4000 rpm and centrifugation time to be about 10 min. The centrifugation may be performed by a device commonly used in the field, such as tubular type centrifuge, etc. After the centrifugation is over, a centrifugal supernatant is collected and filtered by a ceramic membrane with a pore size of 50-200 nm. Such filtration may serve to further screen out macromolecular proteins in the enzymolysis solution, retain the RI, IR and VR peptide segments and increase the mass contents of respective RI, IR and VR peptide segments.

In the present disclosure, a filtrate after the filtration may be subjected to a column chromatography treatment. The column chromatography treatment includes: performing a purification treatment on the filtrate by a cation exchange chromatography column and a hydrophobic chromatography column in sequence. Specifically, the treatment using a cation exchange chromatography column includes: allowing the filtrate to pass through the cation exchange chromatography column at a linear velocity of 1-5 cm/min, and then washing the cation chromatography column with 1-3CV (column volume) of distilled water, subsequently, washing with 1-3CV of 200 mmol/L sodium chloride solution, finally, eluting with 700 mmol/L sodium chloride solution and collecting 2-4 CV of cation eluent; subsequently, allowing the above cation eluent to pass through the hydrophobic chromatography column at a linear velocity of 1-5 cm/min, and then washing the hydrophobic chromatography column with 1-3CV of 700 mmol/L sodium chloride solution to remove impure proteins that are not adsorbed, and finally, eluting the hydrophobic chromatography column with 1-3 CV of distilled water and collecting an eluted liquid.

After the cation exchange chromatography column is regenerated, it may be equilibrated with distilled water, and the packing of the cation exchange chromatography column may use 732 type cation exchange resins, with a particle size of 0.315-1.25 mm. The hydrophobic chromatography column is equilibrated with a sodium chloride solution (700 mmol/L), and the packing of the hydrophobic chromatography column uses Octyl sepharose 4FF type hydrophobic medium, with a particle diameter of 45-165 μm.

Furthermore, the eluent collected from the hydrophobic chromatography column may be concentrated. For example, a rotary evaporator may be used for evaporation and concentration, with a vapor pressure during evaporation of 0.02-0.04 MPa and an evaporation temperature of 60-80° C. When a solid content in the concentrated solution is 10-20%, the concentration will be stopped; and such solid content facilitates a subsequent drying treatment. Specifically, when the solid content is too high, the viscosity of the system will increase, which is not conducive to drying; when the solid content is too low, the energy consumption for drying will increase and the drying time will be prolonged. Furthermore, after concentration, drying may be implemented, so as to obtain the oyster peptide, for example, the drying may be freeze drying. A freeze drying process may include: prefreezing at −50° C. for 4-6 h, and then vacuuming, after the vacuum degree is lower than 20 kPa, increasing the temperature to 20-30° C. and keeping for 15-30 h.

Through the above enzymolysis and separation and purification processes, not only RI, IR and VR peptide segments can be obtained, but also the mass content of the peptide segment RI≥3.60 mg/100 g oyster peptide, the mass content of the peptide segment IR≥7.60 mg/100 g oyster peptide, and the mass content of the peptide segment VR≥6.50 mg/100 g oyster peptide can be obtained through appropriate process parameters.

The present disclosure further provides use of the above oyster peptide in a product for improving sexual function, where the product includes but is not limited to a food product, a health product and a drug.

A large amount of research data demonstrates that the oyster peptide containing functional peptide segments RI, IR and VR with respective specific mass contents according to the present disclosure has a significant ability to promote the generation of testosterone and dihydrotestosterone. It may be considered that the oyster peptide provided by the present disclosure has a significant ability to improve sexual function, and in addition to health care applications in the conventional sense, it can also be used in a product for improving sexual function, etc., thereby broadening the application scope of oysters and providing a new direction for deep processing of oysters.

The implementation of the present disclosure at least has following advantages:

1. The oyster peptide provided by the present disclosure definitely contains the functional peptide segments RI, IR and VR, the mass content of RI being ≥3.60 mg/100 g, the mass content of IR being ≥7.60 mg/100 g, and the mass content of VR being ≥6.50 mg/100 g, and has significant effects in improving sexual function, and can be used as a raw material for a related functional product, thereby providing a broader application prospect for an oyster peptide product.

2. In the preparation method of the oyster peptide provided by the present disclosure, via particular pretreatment, enzymolysis and separation and purification processes, an oyster deep-processing product having peptide segments RI, IR and VR with respective specific mass contents is obtained.

DESCRIPTION OF EMBODIMENTS

Figure 1:
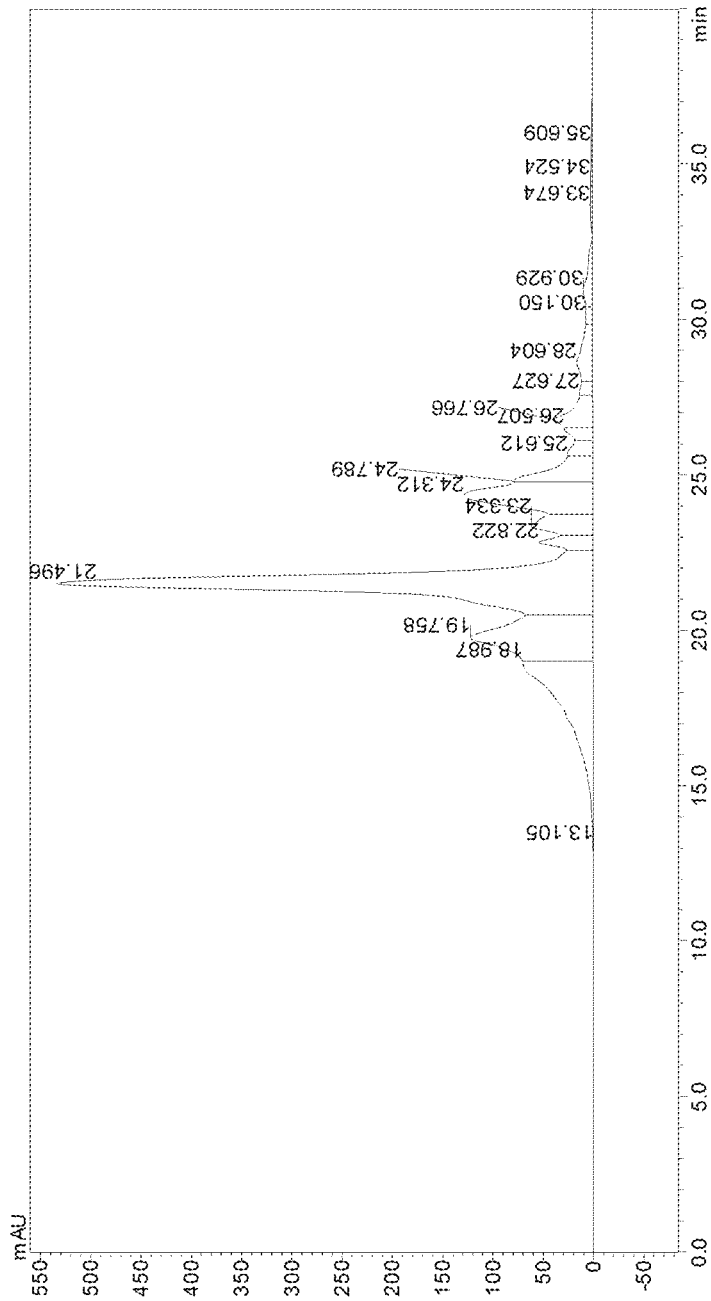
FIG. 1 is a gel chromatogram of molecular weight distribution of the oyster peptide in Example 1 of the present disclosure.

In order to make the objectives, technical solutions and advantages of the present disclosure clearer, the technical solutions in embodiments of the present disclosure will be described clearly and completely with reference to the accompanying drawings in embodiments of the present disclosure. Obviously, the described embodiments are only a part rather than all embodiments of the present disclosure. All other embodiments obtained by persons of ordinary skill in the art based on embodiments of the present disclosure without creative effort shall fall within the protection scope of the present disclosure.

In the following examples and comparative examples, the neutral protease was purchased from Novozymes, 0.8 AU/g; the papain was purchased from Nanning Pangbo, 1 million U/g; the alkaline protease was purchased from Novozymes, 2.4 AU/g; and the acidic protease was purchased from Danisco, 2000 SAPU/g.

Example 1

An oyster peptide of this example was prepared according to the following method.

1. 1 kilogram of shelled oyster meat was taken, thawed and then minced with a mincer to obtain a minced material, and 5 L of distilled water was added to the minced material to prepare a mixed solution. The mixed solution was placed in a water bath of 20° C. and stirred, followed by adding 5 mL of concentrated hydrochloric acid and continuing to stir for 60 min. The resultant solution was subjected to centrifugation with a desk centrifuge at a rotating speed of 3500 rpm for 10 min, and a precipitate was collected.

2. 1 L of distilled water was added to the precipitate, followed by blending and stirring to obtain a slurry. 0.8 g of solid sodium hydroxide was added to the slurry and then the slurry was heated to 90° C. and kept for 60 min under stirring to give a denatured solution of oyster protein.

3. The denatured solution of oyster protein was cooled to 50° C. through a heat exchanger, and subjected to enzymolysis by addition of 1.0 g of the neutral protease and 0.2 g of the papain for 4 h. UHT was utilized to inactivate the enzymes, and an enzymolysis solution was obtained.

4. The enzymolysis solution was centrifuged for 10 min with a desk centrifuge at a rotating speed of 3500 rpm to collect a centrifugal supernatant. The centrifugal supernatant was filtered by a ceramic membrane (200 nm) to collect a filtrate. The filtrate was loaded on a cation exchange chromatography column (column type: xk16-50, column diameter: 16 mm, column height: 400 mm; and packing: 732 type cation exchange resin, with a particle size of 0.315-1.25 mm) at a linear flow rate of 1 cm/min. After being loaded, the cation exchange chromatography column was washed with distilled water at the same flow rate for 60 min and 200 mmol/L sodium chloride solution for 60 min, and eluted with 700 mmol/L sodium chloride solution to collect 400 mL of cation chromatography eluent. The cation chromatography eluent was allowed to pass through a hydrophobic chromatography column (column type: xk16-50, column diameter: 16 mm, column height: 400 mm; packing: Octyl sepharose 4FF type hydrophobic medium, with a particle size of 45-165 μm) at a linear flow rate of 1 cm/min; and then the hydrophobic chromatography column was washed with 700 mmol/L sodium chloride solution for 30 min, and eluted with 300 mL of distilled water to give an hydrophobic chromatography eluent. The hydrophobic chromatography eluent was concentrated to 100 mL with a rotary evaporator (Baume value: 17%), and freeze dried (pre-freezing at −50° C. for 6 hours, vacuuming, and after the vacuum degree was lower than 20 kPa, heating to 20° C. for 20 hours) to give 15 g of oyster peptide powder.

Determination of a Product

1. Detection of Molecular Weight Distribution of the Oyster Peptide

The molecular weight was measured by an experimental method specified in the appendix of GB/T 22492-2008 about soybean peptide powder.

FIG. 1 is a gel chromatogram of molecular weight distribution of the oyster peptide in Example 1 of the present disclosure.

Table 1 shows the molecular weight distribution data of the oyster peptide in Example 1.

TABLE 1

| Range of molecular weight | Start time (min) | End time (min) | Weight-average molecular weight | Peak area percentage (%, λ = 220 nm) |
|---|---|---|---|---|
| 10000 or more | 8.984 | 13.712 | 12221 | 0.0543 |
| 5000-10000 | 13.712 | 15.135 | 6643 | 0.4080 |
| 3000-5000 | 15.135 | 16.184 | 3764 | 0.9609 |
| 2000-3000 | 16.184 | 17.016 | 2425 | 1.5630 |
| 1000-2000 | 17.016 | 18.439 | 1371 | 5.7184 |
| 150-1000 | 18.439 | 22.334 | 353 | 59.7446 |
| 1-150 | 22.334 | 32.621 | 52 | 31.0096 |
| Weight-average molecular weight | | | 413 | |
| Proportion of hydrolysates with relative molecular mass less than 1000 u (%) | | | | 90.75 |

2. Detection of Contents of Functional Peptide Segments RI, IR and VR in the Oyster Peptide Peptide components in the oyster peptide in this example were identified by an ultra-high performance liquid chromatograph Nexera X2 combined with a triple quadrupole mass spectrometer (Shimadzu, Japan).

Condition of liquid chromatography includes: chromatographic column: Inertsil ODS-3 (5 μm, 2.1*250 mm); mobile phase: A: 0.1% formic acid in water, and B: 0.1% formic acid in acetonitrile; gradient elution procedure: 0-15 min, B: 0-50%; 15-20 min, B: 50-100%; 20-25 min, B: 100%; 25.1-35 min, B: 0%; flow rate: 0.2 mL/min; injection volume: 1 μL; column temperature: 40° C.

Condition of mass spectrometry includes: ionization mode: ESI, positive ion mode; ionspray voltage: +4.5 kV; flow rate of atomizing gas: 3.0 L/min, nitrogen; flow rate of heating gas: 10 L/min, nitrogen; flow rate of drying gas: 10 L/min, nitrogen; desolvation line (DL) temperature: 250° C.; heating module temperature: 400° C.; ion source temperature: 300° C.; scan mode: multiple reaction monitoring (MRM); residence time: 100 ms; delay time: 3 ms; MRM parameter: see Table 2.

TABLE 2

| Analyte | Precursor ion | Production | Q1 Pre Bias (V) | CE (V) | Q3 Pre Bias (V) |
|---|---|---|---|---|---|
| RI | 288 | 70* | −14 | −26 | −18 |
| | | 86 | −11 | −18 | −19 |
| IR | 288 | 175* | −11 | −24 | −10 |
| | | 86 | −11 | −19 | −19 |
| VR | 274 | 175* | −13 | −28 | −15 |
| | | 72 | −11 | −19 | −19 |

*denotes quantitative ion.

Preparation of a peptide segment standard: 20.0 mg of RI, IR and VR standard powders were weighed respectively and accurately, dissolved in MilliQ water (purchased from Millipore), vortexed for mixing uniformly, and diluted with MilliQ water to 100 mL to obtain solutions, that was, standard stock solutions of 200 μg/mL. 500 μL of the above standard stock solutions were taken respectively, mixed and diluted with MilliQ water to 10 mL, and a mixed standard mother solution in 10 μg/mL was obtained. The above mixed standard mother solution was gradually diluted with MilliQ water to a series of standard working solutions in 0.0625, 0.125, 0.25, 0.5, 1, 2.5, 5 and 10 μg/mL.

Figure 2:
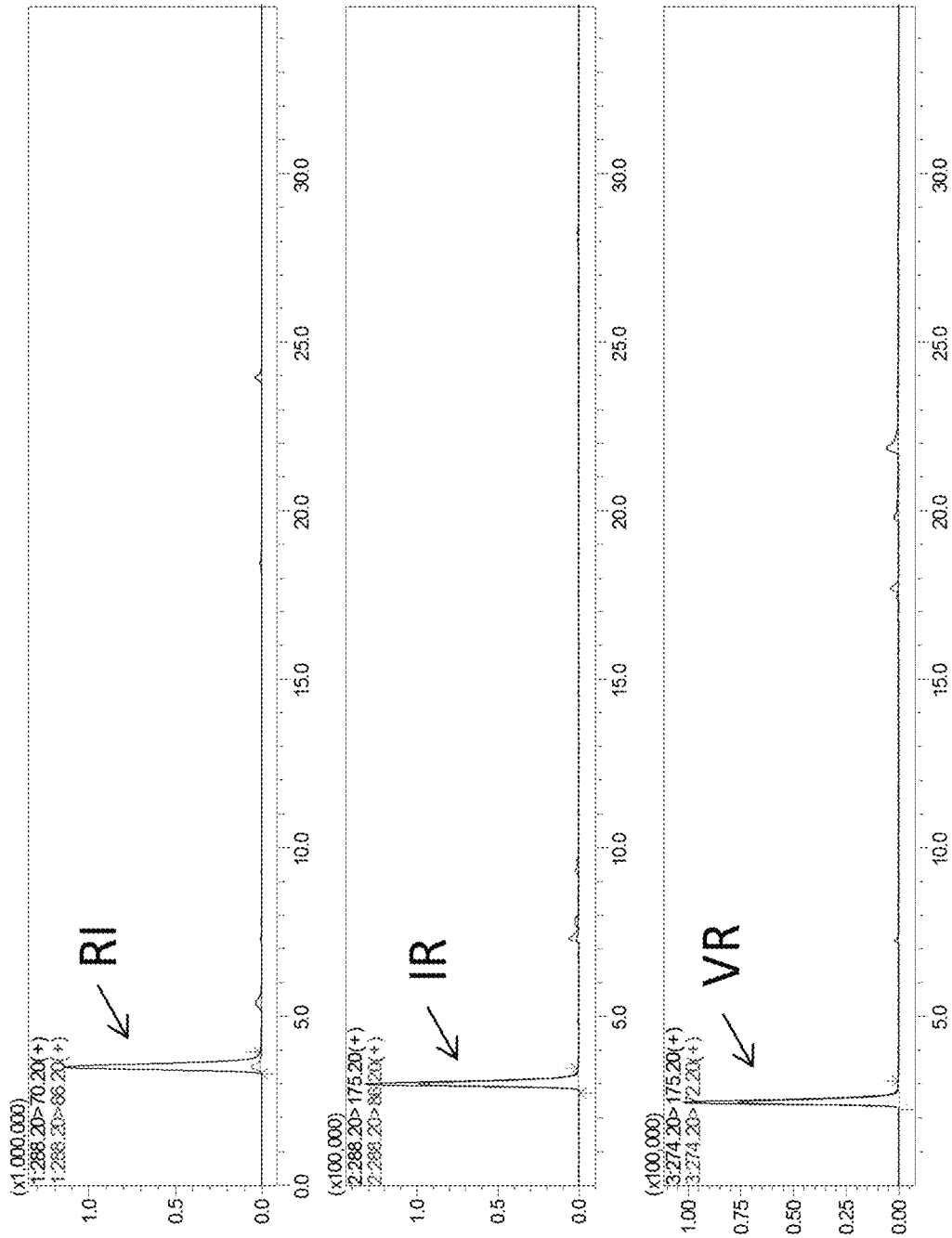
FIG. 2 is a mass spectrogram of 1 μg/mL standard sample for identification of RI, IR and VR in examples and comparative examples of the present disclosure.
Figure 3:
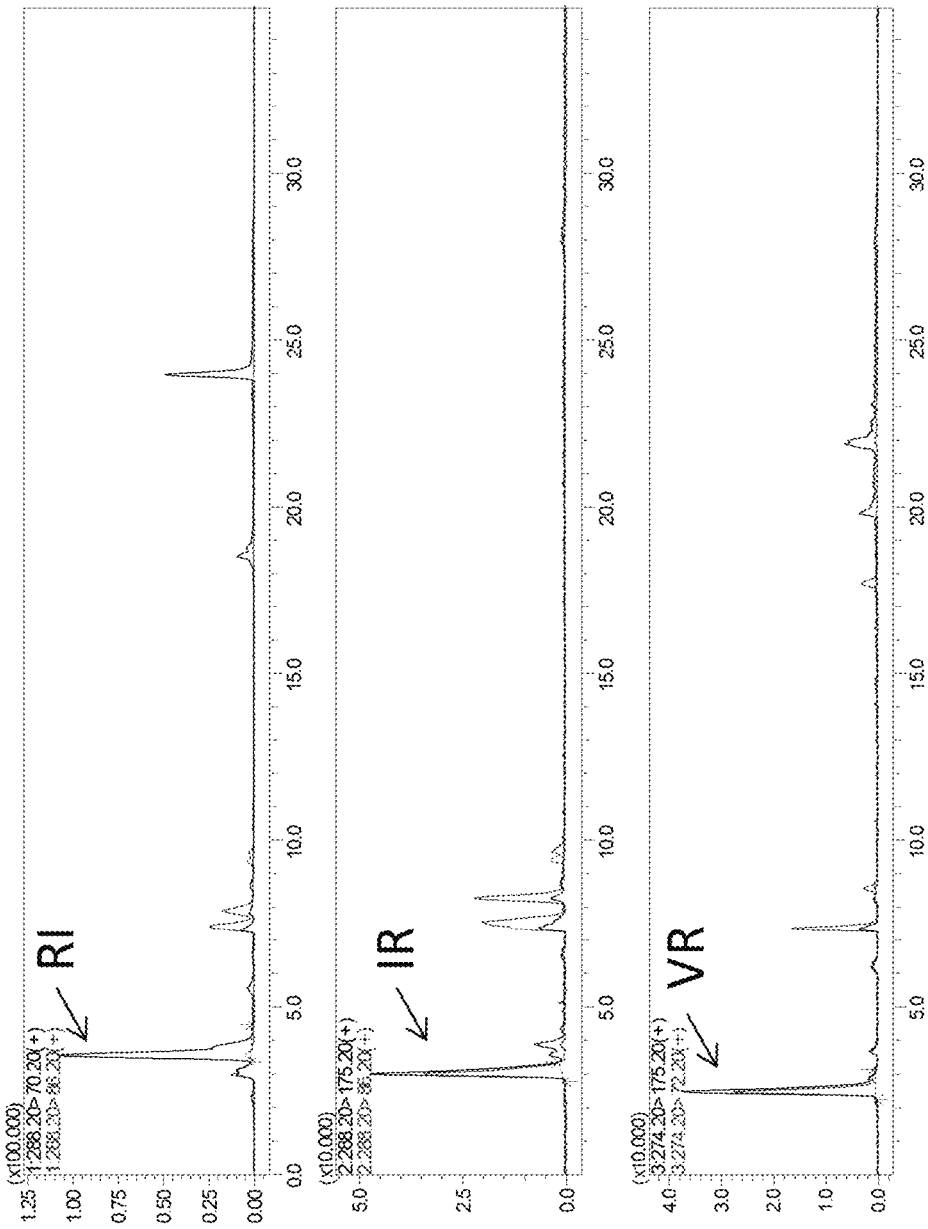
FIG. 3 is a mass spectrogram of RI, IR and VR in the oyster peptide (3 mg/mL) in Example 1 of the present disclosure.

FIG. 2 is a mass spectrogram of 1 μg/mL standard sample for identification of RI, IR and VR in examples and comparative examples of the present disclosure; and FIG. 3 is a mass spectrogram of RI, IR and VR in the oyster peptide in Example 1 (3 mg/mL) of the present disclosure.

Based on the comparison of FIG. 3 and FIG. 2, it can be seen that the peptide segments RI, IR, and VR existed in the oyster peptide in Example 1 at the same time. After detection, in the oyster peptide prepared in Example 1, the content of the RI was 3.68 mg/100 g, the content of the IR was 7.84 mg/100 g, and the content of the VR was 6.77 mg/100 g.

Example 2

An oyster peptide of this example was prepared according to the following method.

1. 5 kilogram of shelled oyster meat was taken, thawed and then minced with a mincer to obtain a minced material, and 25 L of distilled water was added to the minced material to prepare a mixed solution. The mixed solution was placed in a water bath of 20° C. and stirred, followed by adding 25 mL of concentrated hydrochloric acid and continuing to stir for 60 min. The resultant solution was subjected to centrifugation with a desk centrifuge at a rotating speed of 3500 rpm for 10 min, and a precipitate was collected.

2. 5 L of distilled water was added to the precipitate, followed by blending and stirring to obtain a slurry. 5 g of solid sodium hydroxide was added to the slurry and then the slurry was heated to 90° C. and kept for 60 min under stirring to give a denatured solution of oyster protein.

3. The denatured solution of oyster protein was cooled to 50° C. through a heat exchanger, and subjected to enzymolysis by addition of 5 g of the neutral protease and 1 g of the papain for 5 h. UHT was utilized to inactivate the enzymes, and an enzymolysis solution was obtained.

4. The enzymolysis solution was centrifuged for 10 min with a desk centrifuge at a rotating speed of 3500 rpm to collect a centrifugal supernatant. The centrifugal supernatant was filtered by a ceramic membrane (200 nm) to collect a filtrate. The filtrate was loaded on a cation exchange chromatography column (column type: xk26-100, column diameter: 26 mm, column height: 60 mm; and packing: 732 type cation exchange resin, with a particle size of 0.315-1.25 mm) at a linear flow rate of 5 cm/min. After being loaded, the cation exchange chromatography column was washed with distilled water at the same flow rate for 30 min and 200 mmol/L sodium chloride solution for 30 min, and eluted with 700 mmol/L sodium chloride solution to collect 1500 mL of cation chromatography eluent. The cation chromatography eluent was allowed to pass through a hydrophobic chromatography column (column type: xk26-100, column diameter: 26 mm, column height: 60 mm; packing: Octyl sepharose 4FF type hydrophobic medium, with a particle size of 45-165 μm) at a linear flow rate of 5 cm/min; and then the hydrophobic chromatography column was washed with 700 mmol/L sodium chloride solution for 30 min, and eluted with 1600 mL of distilled water to give an hydrophobic chromatography eluent. The hydrophobic chromatography eluent was concentrated to 400 mL with a rotary evaporator (Baume value: 18%), and freeze dried (pre-freezing at −50° C. for 6 hours, then vacuuming, and after the vacuum degree was lower than 20 kPa, and heating to 20° C. for 20 hours) to give 70 g of oyster peptide powder.

Determination of a Product

1. The molecular weight distribution of the oyster peptide in this example was detected by the same method as that in Example 1.

Figure 4:
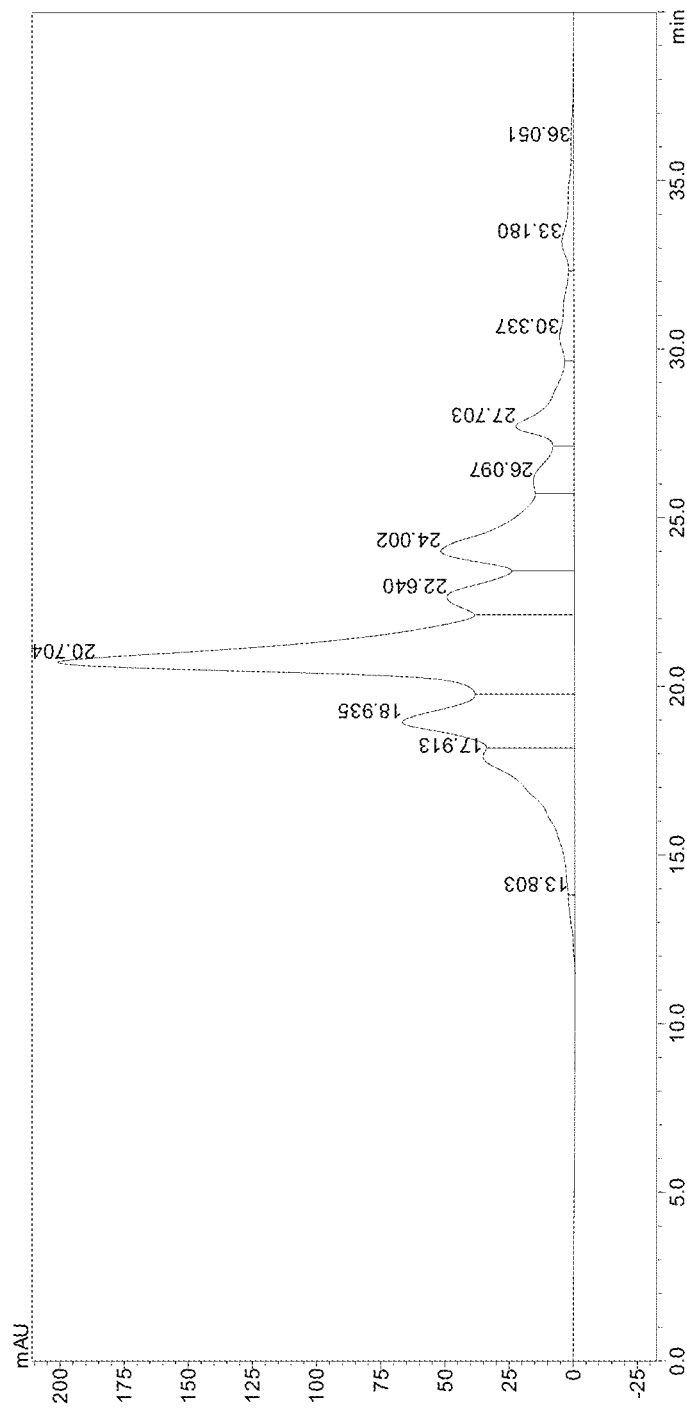
FIG. 4 is a gel chromatogram of molecular weight distribution of the oyster peptide in Example 2 of the present disclosure.

FIG. 4 is a gel chromatogram of molecular weight distribution of the oyster peptide in Example 2 of the present disclosure.

Table 3 shows the molecular weight distribution data of the oyster peptide in Example 2.

TABLE 3

| Range of molecular weight | Start time (min) | End time (min) | Weight-average molecular weight | Peak area percentage (%, $\lambda$ = 220 nm) |
|---|---|---|---|---|
| 10000 or more | 7.993 | 12.850 | 12241 | 0.1186 |
| 5000-10000 | 12.850 | 14.312 | 6891 | 0.6045 |
| 3000-5000 | 14.312 | 15.390 | 3809 | 0.7980 |
| 2000-3000 | 15.390 | 16.245 | 2411 | 1.2397 |
| 1000-2000 | 16.245 | 17.707 | 1352 | 5.2243 |
| 150-1000 | 17.707 | 21.709 | 355 | 54.2861 |
| 150 or less | 21.709 | 32.278 | 56 | 35.8724 |
| Weight-average molecular weight | | | 400 | |
| Proportion of hydrolysates with relative molecular mass less than 1000 u (%) | | | 90.16 | |

2. The contents of functional peptide segments RI, IR and VR in the oyster peptide were detected by the same method as that in Example 1.

Figure 5:
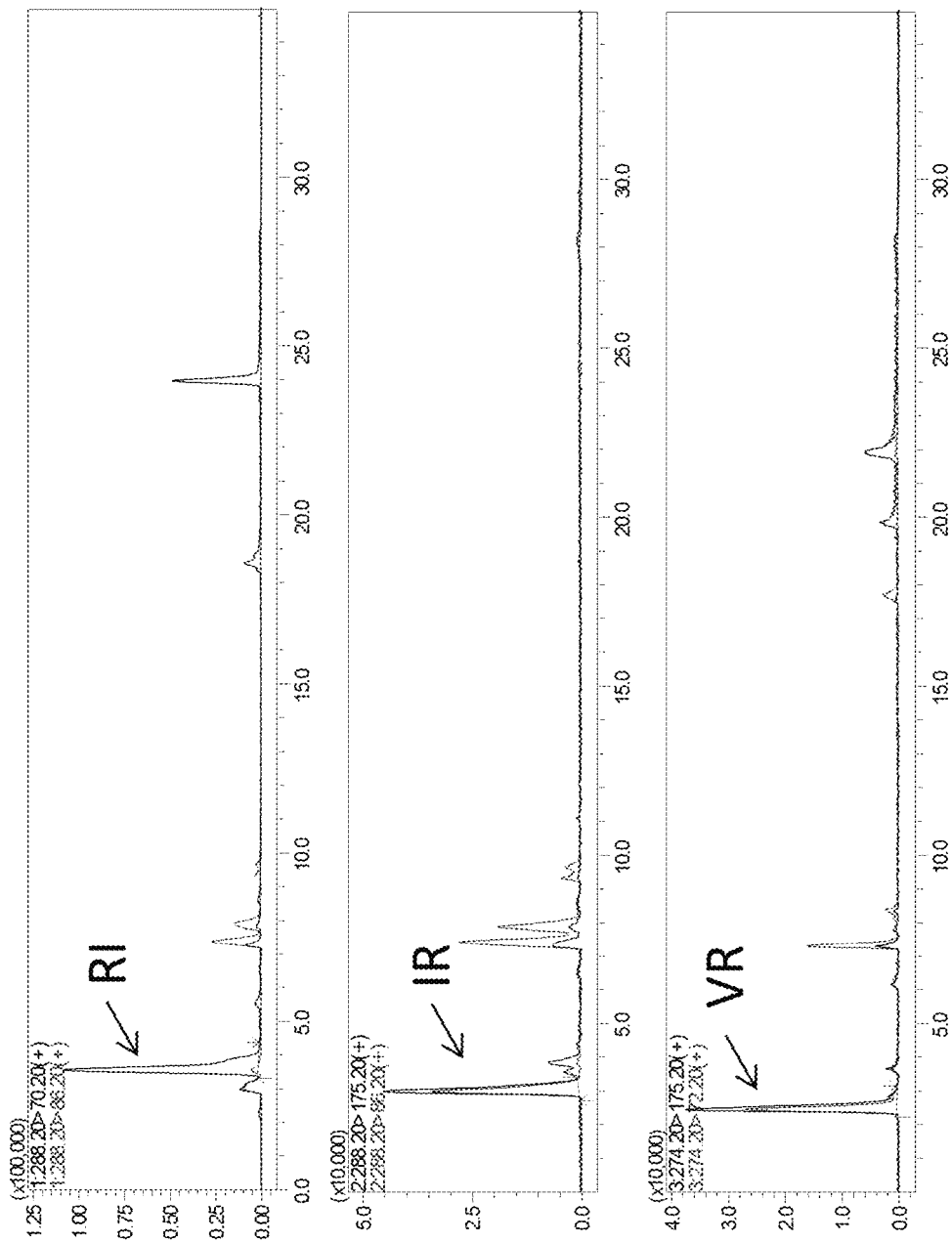
FIG. 5 is a mass spectrogram of RI, IR and VR in the oyster peptide (3 mg/mL) in Example 2 of the present disclosure.

FIG. 5 is a mass spectrogram of RI, IR and VR in the oyster peptide in Example 2 (3 mg/mL) of the present disclosure.

Based on the comparison of FIG. 5 and FIG. 2, it can be seen that the peptide segments RI, IR, and VR existed in the oyster peptide in Example 2 at the same time. After detection, in the oyster peptide prepared in Example 2, the content of the RI was 3.75 mg/100 g, the content of the IR was 7.69 mg/100 g, and the content of the VR was 6.87 mg/100 g.

Example 3

1. 10 kg of shelled oyster meat was taken, thawed and then minced with a mincer to obtain a minced material, and 50 L of distilled water was added to the minced material to prepare a mixed solution. The mixed solution was placed in a water bath of 25° C., and stirred, followed by adding 50 mL of concentrated hydrochloric acid and continuing to stir for 60 min. The resultant solution was subjected to centrifugation with a desk centrifuge at a rotating speed of 3500 rpm for 10 min, and a precipitate was collected.

2. 10 L of distilled water was added to the precipitate, followed by blending and stirring to obtain a slurry. 10 g of solid sodium hydroxide was added to the slurry and then the slurry was heated to 90° C. and kept for 90 min under stirring to give a denatured solution of oyster protein.

3. The denatured solution of oyster protein was cooled to 50° C. through a heat exchanger, and subjected to enzymolysis by addition of 12 g of the neutral protease and 2 g of the papain for 5 h. UHT was utilized to inactivate the enzymes, and an enzymolysis solution was obtained.

4. The enzymolysis solution was centrifuged for 10 min with a desk centrifuge at a rotating speed of 3500 rpm to collect a centrifugal supernatant. The centrifugal supernatant was filtered by a ceramic membrane (200 nm) to collect a filtrate. The filtrate was loaded on a cation exchange chromatography column at a linear flow rate of 1 cm/min. After being loaded, the cation exchange chromatography column was washed with distilled water at the same flow rate for 60 min and 200 mmol/L sodium chloride solution for 60 min, and eluted with 700 mmol/L sodium chloride solution to collect 3000 mL of cation chromatography eluent. The cation chromatography eluent was allowed to pass through a hydrophobic chromatography column at a linear flow rate of 1 cm/min; and then the hydrophobic chromatography column was washed with 700 mmol/L sodium chloride solution for 30 min, and eluted with 3000 mL of distilled water, so as to give a hydrophobic chromatography eluent. The hydrophobic chromatography eluent was concentrated to 800 mL with a rotary evaporator (Baume value: 19%), and freeze dried (pre-freezing at −50° C. for 6 hours, vacuuming, and after the vacuum degree was lower than 20, heating to 20° C. for 20 hours) to give 150 g of oyster peptide powder. In this case, a type of the chromatography column is XK50/400.

Determination of a Product

1. The molecular weight distribution of the oyster peptide in this example was detected by the same method as that in Example 1.

Figure 6:
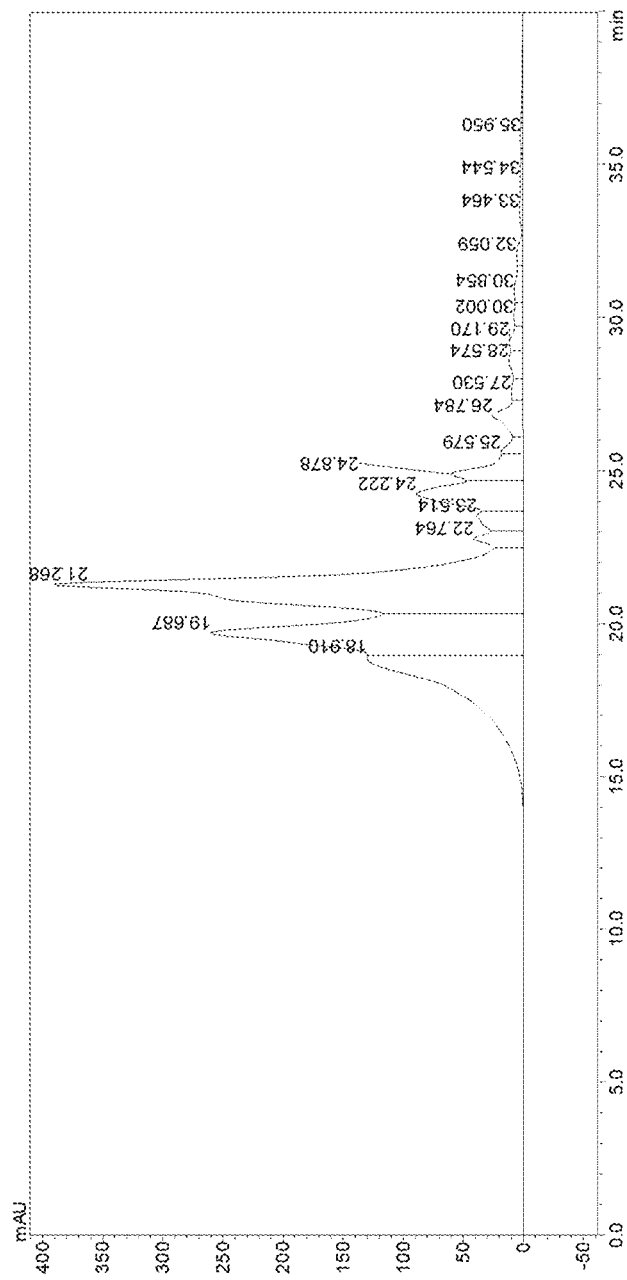
FIG. 6 is a gel chromatogram of molecular weight distribution of the oyster peptide in Example 3 of the present disclosure.

FIG. 6 is a gel chromatogram of molecular weight distribution of the oyster peptide in Example 3 of the present disclosure.

Table 4 shows the molecular weight distribution data of the oyster peptide in Example 3.

TABLE 4

| Range of molecular weight | Start time (min) | End time (min) | Weight-average molecular weight | Peak area percentage (%, $\lambda$ = 220 nm) |
|---|---|---|---|---|
| 10000 or more | 8.939 | 13.648 | 11045 | 0.0023 |
| 5000-10000 | 13.648 | 15.065 | 6198 | 0.1521 |
| 3000-5000 | 15.065 | 16.110 | 3706 | 0.7952 |
| 2000-3000 | 16.110 | 16.939 | 2409 | 1.6510 |
| 1000-2000 | 16.939 | 18.356 | 1346 | 7.6893 |
| 150-1000 | 18.356 | 22.236 | 426 | 67.9874 |
| 150 or less | 22.236 | 32.482 | 51 | 20.8760 |
| Weight-average molecular weight | | | 483 | |
| Proportion of hydrolysates with relative molecular mass less than 1000 u (%) | | | 88.86 | |

2. The contents of functional peptide segments RI, IR and VR in the oyster peptide were detected by the same method as that in Example 1.

Figure 7:
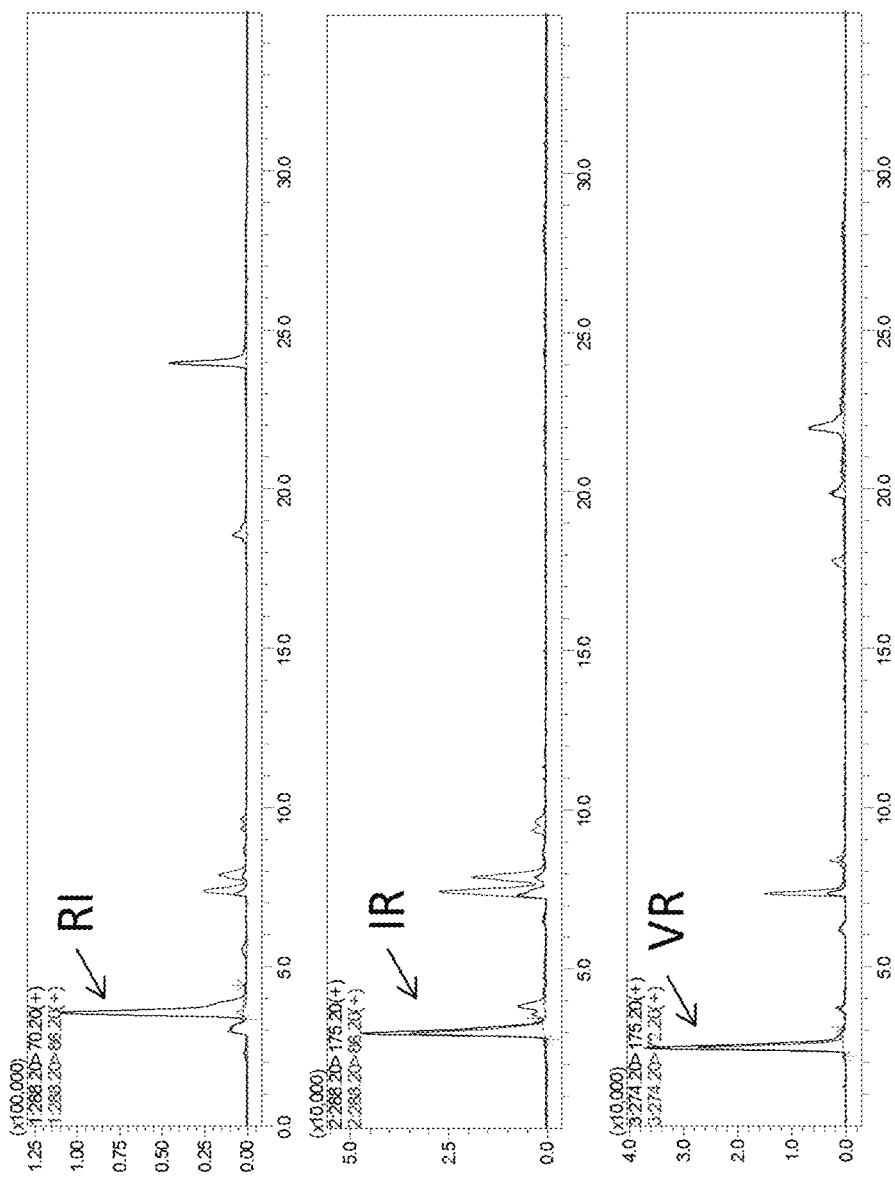
FIG. 7 is a mass spectrogram of RI, IR and VR in the oyster peptide (3 mg/mL) in Example 3 of the present disclosure.

FIG. 7 is a mass spectrogram of RI, IR and VR in the oyster peptide in Example 3 (3 mg/mL) of the present disclosure.

Based on the comparison of FIG. 7 and FIG. 2, it can be seen that the peptide segments RI, IR, and VR existed in the oyster peptide in Example 3 at the same time. After detection, in the oyster peptide prepared in Example 3, the content of the RI was 3.78 mg/100 g, the content of the IR was 7.86 mg/100 g, and the content of the VR was 6.63 mg/100 g.

Comparative Example 1

The preparation method of this comparative example was basically the same as that in Example 2, and the only difference was that: in this comparative example, after the centrifugal supernatant was filtered by a 200 nm ceramic membrane, the filtrate was directly concentrated to 800 mL with a rotary evaporator without treatments of a cation exchange chromatography column and a hydrophobic chromatography column, and freeze dried, giving 160 g of oyster peptide powder.

Determination of a Product

1. The contents of functional peptide segments RI, IR and VR in the oyster peptide were detected by the same method as that in Example 1.

Figure 8:
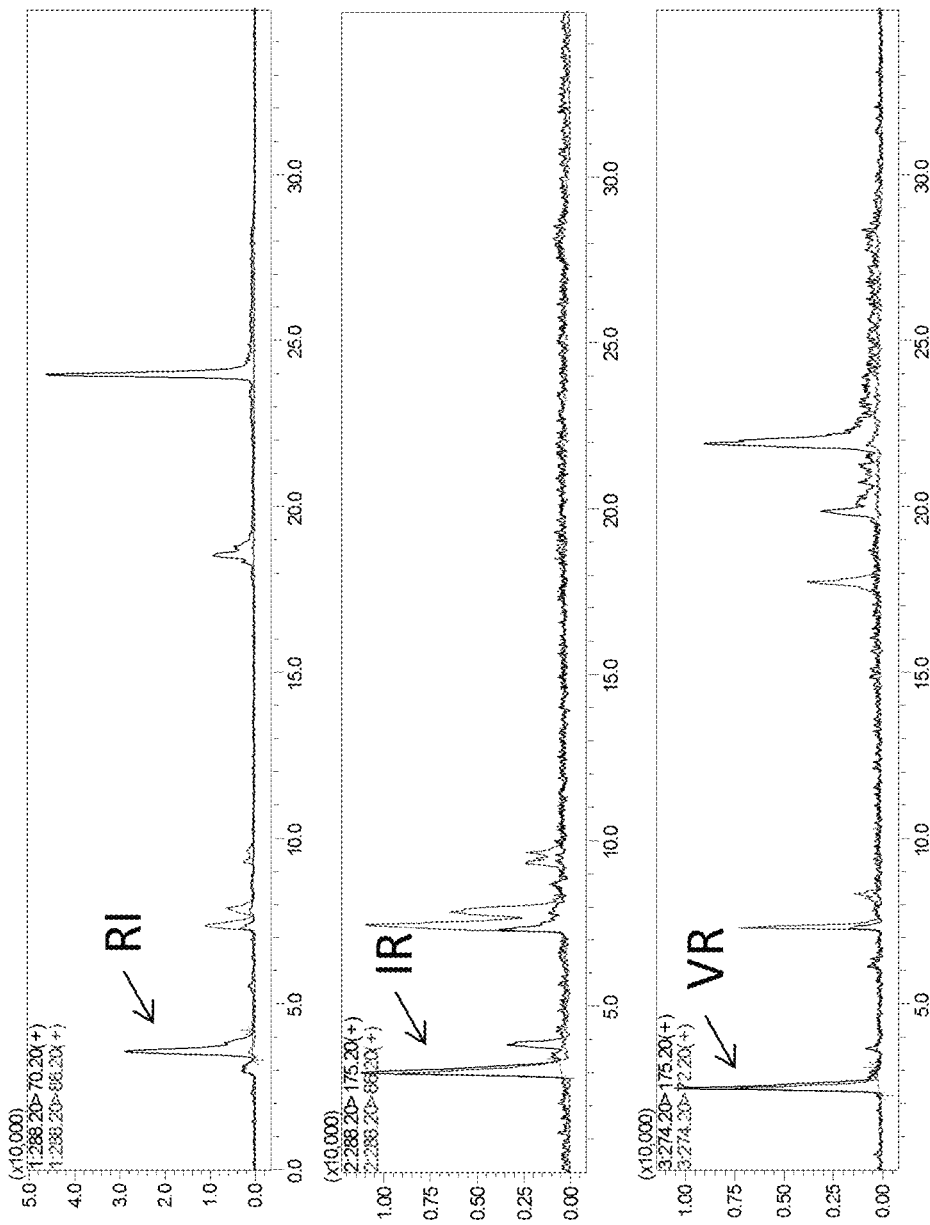
FIG. 8 is a mass spectrogram of RI, IR and VR in the oyster peptide (3 mg/mL) in Comparative Example 1 of the present disclosure.

FIG. 8 is a mass spectrogram of RI, IR and VR in the oyster peptide in Comparative Example 1 (3 mg/mL) of the present disclosure.

Based on the comparison of FIG. 8 and FIG. 2, it can be seen that the peptide segments RI, IR, and VR existed in the oyster peptide in this Comparative Example 1 at the same time. After detection, in the oyster peptide prepared in the Comparative Example 1, the content of the RI was 1.13 mg/100 g, the content of the IR was 2.14 mg/100 g, and the content of the VR was 1.95 mg/100 g.

Comparative Example 2

The preparation method of this comparative example was basically the same as that in Example 2, and the only difference was that: in this comparative example, after 1500 mL of eluent from a cation exchange chromatography column was collected, 1500 mL of eluent was directly concentrated to 700 mL with a rotary evaporator without a treatment of a hydrophobic chromatography column, and freeze dried, giving 140 g of oyster peptide powder.

Determination of a Product

1. The contents of functional peptide segments RI, IR and VR in the oyster peptide were detected by the same method as that in Example 1.

Figure 9:
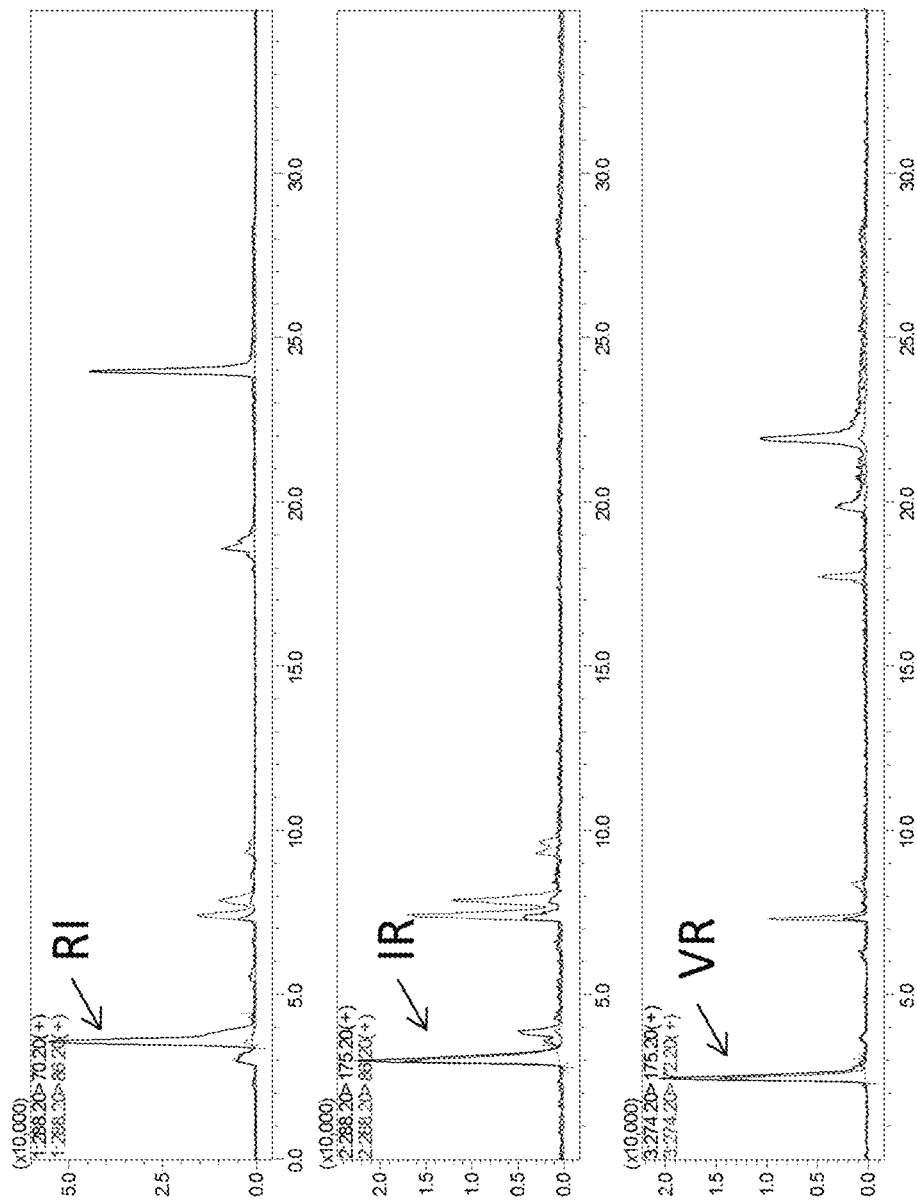
FIG. 9 is a mass spectrogram of RI, IR and VR in the oyster peptide (3 mg/mL) in Comparative Example 2 of the present disclosure.

FIG. 9 is a mass spectrogram of RI, IR and VR in the oyster peptide in Comparative Example 2 (3 mg/mL) of the present disclosure.

Based on the comparison of FIG. 9 and FIG. 2, it can be seen that the peptide segments RI, IR, and VR existed in the oyster peptide in this Comparative Example 2 at the same time. After detection, in the oyster peptide prepared in this Comparative Example 2, the content of the RI was 1.85 mg/100 g, the content of the IR was 3.79 mg/100 g, and the content of the VR was 3.25 mg/100 g.

Comparative Example 3

The preparation method of this comparative example was basically the same as that in Example 2, and the only difference was that: 5 g of alkaline protease (Novozymes, Alcalase 2.4 L) and 5 g of neutral protease (Novozymes, Neutrase 0.8 L) were added for the enzymolysis, the enzymolysis time was 4 h, and other post-processing steps were the same as those in Example 2.

Determination of a Product

1. The contents of functional peptide segments RI, IR and VR in the oyster peptide were detected by the same method as that in Example 1.

Figure 10:
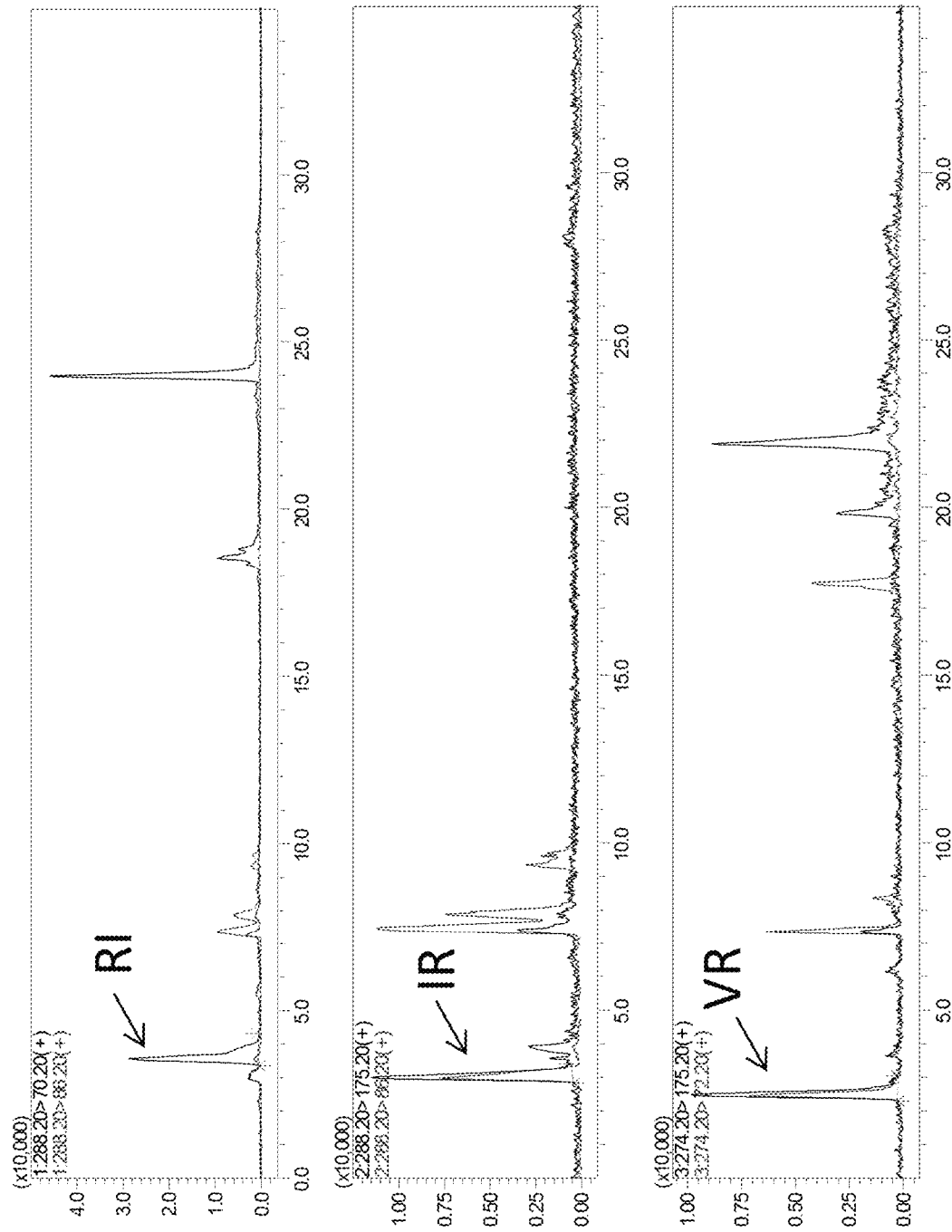
FIG. 10 is a mass spectrogram of RI, IR and VR in the oyster peptide (3 mg/mL) in Comparative Example 3 of the present disclosure.

FIG. 10 is a mass spectrogram of RI, IR and VR in the oyster peptide in Comparative Example 3 (3 mg/mL) of the present disclosure.

Based on the comparison of FIG. 10 and FIG. 2, it can be seen that the peptide segments RI, IR, and VR existed in the oyster peptide in this Comparative Example 3 at the same time. After detection, in the oyster peptide prepared in this Comparative Example 3, the content of the RI was 0.87 mg/100 g, the content of the IR was 2.08 mg/100 g, and the content of the VR was 1.62 mg/100 g.

Comparative Example 4

The preparation method of this comparative example was basically the same as that in Example 2, and the only difference was that: a slurry obtained by washing with water and blending was subjected to enzymolysis using 5 g of acidic protease (Danisco, FOODPRO PAL) and 1 g of papain for 4 h without adding NaOH, and other post-processing steps were the same as those in Example 2.

Determination of a Product

1. The contents of functional peptide segments RI, IR and VR in the oyster peptide were detected by the same method as that in Example 1.

Figure 11:
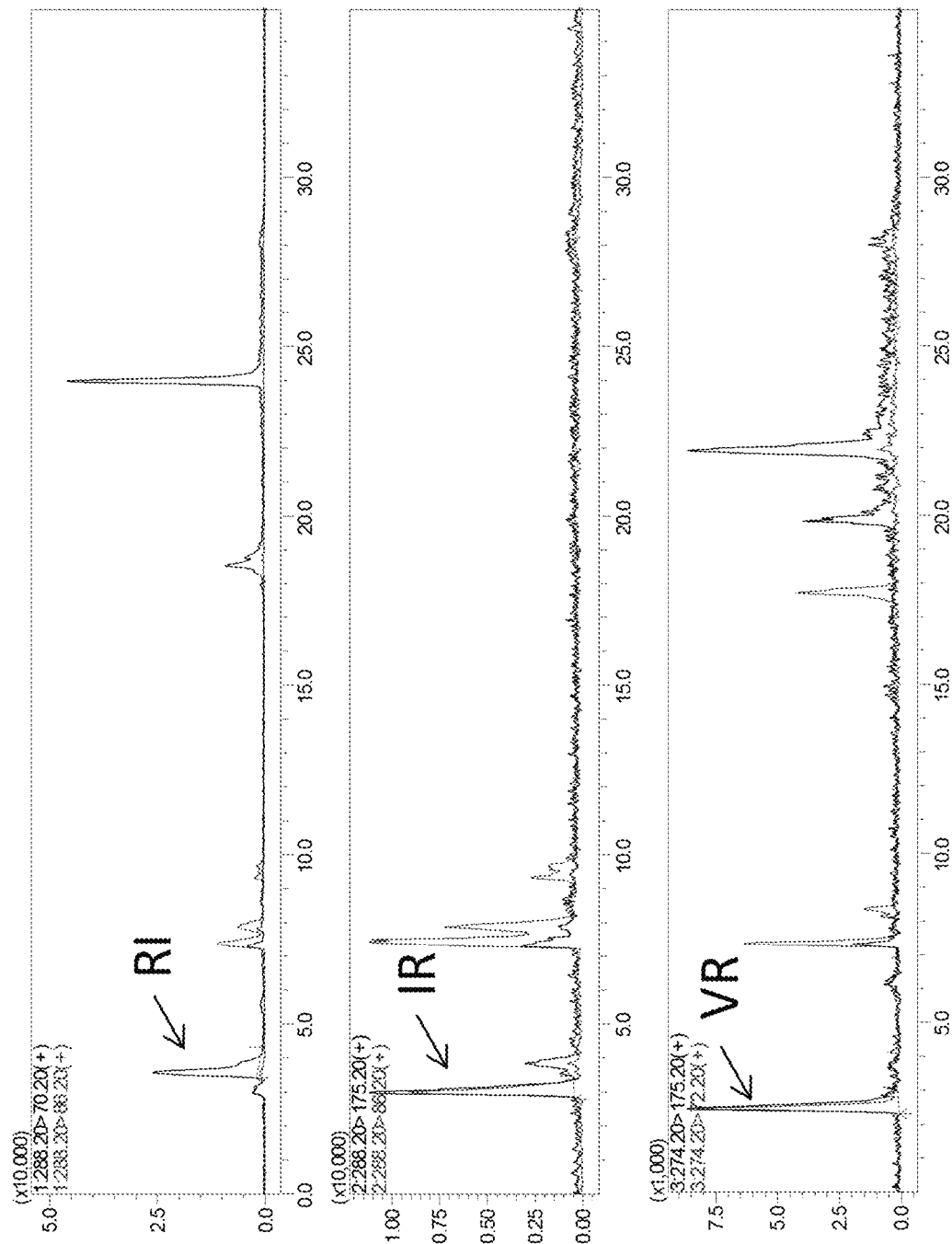
FIG. 11 is a mass spectrogram of RI, IR and VR in the oyster peptide (3 mg/mL) in Comparative Example 4 of the present disclosure.

FIG. 11 is a mass spectrogram of RI, IR and VR in the oyster peptide in Comparative Example 4 (3 mg/mL) of the present disclosure.

Based on the comparison of FIG. 11 and FIG. 2, it can be seen that the peptide segments RI, IR, and VR existed in the oyster peptide in this Comparative Example 4 at the same time. After detection, in the oyster peptide prepared in this Comparative Example 4, the content of the RI was 0.75 mg/100 g, the content of the IR was 1.63 mg/100 g, and the content of the VR was 1.30 mg/100 g.

The capacity of samples for improving sexual function was evaluated by the following methods.

1. An MTT Method was Used to Detect the Effect of the Oyster Peptide on the Proliferation of Testicular Interstitial Cells TM3.

MTT operation procedure: the cell density was diluted to $1\times10^5$ cells/mL, and cells were added to a 96-well plate in 100 μL/well. After cells were observed to adhere evenly over 24 hours, a supernatant was discarded, PBS buffer was added to wash the cells for 2-3 times, and the cells were treated with a cell culture solution containing the oyster peptide; where, wells without sample were set as a normal control group. In the same 96-well plate, each concentration gradient was provided with 4 duplicate wells; after 24 hours, the cell supernatant was discarded, PBS buffer was used to wash the cells for 2-3 times, and then 100 μL of MTT solution (0.5 mg/mL) was added to each well for further incubating at 37° C. for 4 h, the culture solution and MTT were removed carefully, and 100 μL of DMSO solution was added to each well and subjected to shaking for 10 minutes to dissolve crystals. A microplate reader was used to measure absorbance, i.e. optical density (OD), at 490 nm, and Cell survival rate (%)=Experimental group OD/Control OD×100%.

2. Detection of Testosterone

TM3 cells were cultured with an oyster peptide culture solution for 24 h, the obtained culture solution was centrifuged, a supernatant was taken and mixed uniformly, and the content of testosterone was detected according to instructions of ELISA kit.

Operation procedure for detecting testosterone: (1) Plates required for test were taken out from a sealed aluminum foil bag that had been equilibrated to room temperature; unused plates and a desiccant were returned into the aluminum foil bag, and the bag was sealed by fastening with a self-sealing strip and then placed at 2-8° C. (2) Standards and samples to be tested were added to all wells of an ELISA plate at 50 μL/well, and 4 Blank wells were set. (3) After addition of 50 μL of enzyme-labeled antigen working solution to each well (except the blank wells), 50 μL of rabbit anti-testosterone antibody working solution was added in the same loading sequence and mixed uniformly, and then reaction wells were sealed with a plate-sealing film and incubated at 37° C. for 1 h. (4) The microplate reader was powered on 20 minutes in advance, so as to preheat the instrument and set a detection program. (5) The plate-sealing film was removed carefully; a plate washer was used for washing the plate for 3 times, drying as much as possible for the last time. (6) Based on the actual amount in the experiment, a chromogenic substrate A and a chromogenic substrate B were mixed in equal volumes, the obtained mixture was added to the used wells at 100 μL/well, the reaction wells were sealed with the plate-sealing film, and incubation was conducted away from light at 37° C. for 15 min. (7) A stop solution was added at 50 μL/well and mixed uniformly and then the $OD_{450}$ value was measured (within 10 min).

3. Dihydrotestosterone (DHT) Content

TM3 cells was cultured with the oyster peptide culture solution for 24 h, the obtained culture solution was centrifuged, a supernatant was taken and mixed uniformly, and the content of dihydrotestosterone was detected according to instructions of ELISA kit.

Operation procedure for detecting dihydrotestosterone: (1) Standards were added into standard wells at 50 μL/well. (2) 40 μL of sample diluent was added to sample wells and then 10 μL of the sample to be tested was added, and nothing was added to the blank wells. (3) The reaction wells were sealed with the plate-sealing film and incubated at 37° C. for 45 min. (4) The plate-sealing film was removed carefully; a plate washer was used for washing the plate for 3 times, drying as much as possible for the last time. (5) 50 μL of antibody was added to each well except blank wells. (6) The reaction wells were sealed with the plate-sealing film and incubated at 37° C. for 30 min. (7) The reaction wells were sealed with the microplate sealing film and incubated at 37° C. for 30 min. (8) The washing steps were the same as that in (5). (9) 50 μL of chromogenic solution A and 50 μL of chromogenic solution B were added to each well and mixing gently; and incubation was conducted away from light at 37° C. for 15 min. (10) A stop solution was added at 50 μL/well and mixed uniformly and then the $OD_{450}$ value was measured.

4. Detection of NO Content

TM3 cells were cultured with the oyster peptide culture solution for 24 h, the obtained culture solution was centrifuged, a supernatant was taken and mixed uniformly, and the content of NO was detected according to instructions of NO determination kit.

Operation procedure for detecting NO: (1) Reagent preparation: all reagents were taken out and equilibrated to room temperature for use. (2) 100 μM standard working solution: 5 μL of concentrated standard was added to 495 μL of reaction buffer and mixed well. (3) Preparation of a working solution for detection of total nitric oxide: based on the number of samples, 1 volume of $NO_3$-reductant and 40 volumes of Griess Reagent II were added to 40 volumes of Griess Reagent I and mixed well to prepare a proper amount of reaction working solution, which was needed to be used within 1 hour. (4) Number and add samples to wells in a 96-well plate: the microplate was sealed by the plate-sealing film, and incubated at 60° C. for 10 min. After the incubation was over, the microplate was taken out, placed into an incubator at 37° C. and further incubated for 60 min, and then taken out and placed into a microplate reader for reading at 540 nm. (5) Quantitative calculation of total nitric oxide in samples:

Total nitric oxide content in sample (μM) =

$(OD$ value of sample wells $- OD$ value of blank wells$)/$
$(OD$ value of standard wells $- OD$ value of blank wells$) \times$
standard concentration (100 μM) $\times n$ (dilution factor).

5. Detection of SOD (Superoxide Dismutase) Content in Mouse Testicular Interstitial Cells TM3

TM3 cells were cultured with the oyster peptide culture solution for 24 h, and lysed to obtain a lysate. The content of SOD was detected according to the instructions of SOD determination kit.

Operation procedure for detecting SOD: (1) Approximately $2 \times 10^6$ cells (800 g) were collected, and centrifuged at 4° C. for 2 min; a supernatant was discarded, cold PBS was used to wash the obtained cells, and a supernatant was discarded after centrifugation to collect precipitate; 500 μL of pre-cooled lysate (50 mM Potassium phosphate, 0.1 mM EDTA, 0.5% Triton X-100) was added the precipitate to resuspend cells, followed by standing on ice for 10 min and then centrifuging at 12000 g at 4° C. for 5 min; and a supernatant was taken for testing. (2) Wells in a 96-well plate were numbered and loaded with samples; after being loaded, a microplate was incubated at room temperature for 10 min. After the incubation was over, the microplate was taken out, and placed into a microplate reader for reading the optical density at 550 nm. (3) Quantitative calculation of superoxide dismutase (SOD) in sample was as follows: Inhibition rate (%)=(OD value of control wells−OD value of sample wells)/OD value of control wells. In the event that the enzyme activity when the inhibition rate is 50% was defined as 1 U, superoxide dismutase (SOD) content in the supernatant of the cell lysate (U/mg)=Inhibition rate/50%/ Protein concentration of the sample to be detected (mg/ mL)×100×n (dilution factor).

6. Detection of cGMP (Cyclic Guanosine Monophosphate)

TM3 cells were cultured with the oyster peptide culture solution for 24 h, and lysed to obtain a lysate. The content of cGMP was detected according to the instructions of cGMP determination kit.

Operation procedure for detecting cGMP: (1) Plates required for test were taken out from a sealed aluminum foil bag that had been equilibrated to room temperature, unused plates and a desiccant were returned into the aluminum foil bag, and the bag was sealed by fastening with a self-sealing strip and placed at 2-8° C. (2) Neutralization reagent was added to all wells of an ELISA plate at 50 μL/well. (2) Subsequently, appropriate wells were selected and added with standards and samples to be tested, at 100 μL/well. (3) 50 μL of cGMP conjugate was added to each well, and then 50 μL of cGMP ELISA antibody was added. (4) After mixing uniformly, reaction wells were sealed with a plate-sealing film, and placed on a plate shaker at 500 rpm for incubation for 2 h. (5) The plate-sealing film was removed carefully; a plate washer was used for washing the plate for 3 times, drying as much as possible for the last time. (6) Subsequently, 200 μL of pNpp substrate solution was added to each well, and incubated for 1 h at room temperature. (7) Finally, 50 μL of stop solution was added to each well and mixing uniformly, and then the $OD_{450}$ value was measured (within 10 min).

The oyster peptides in Examples 1-3 and the oyster peptides in Comparative Examples 1-4 were used as samples to implement the following tests.

Test Example 1 a. In order to detect the effect of different concentrations of the oyster peptide culture solution on the activity of TM3 cells, a series of concentrations of 100 μg/mL, 200 μg/mL, 400 μg/mL, 800 μg/mL, 1 mg/mL, 2 mg/mL, 4 mg/mL, 8 mg/mL, and 10 mg/mL of the oyster peptide culture solution of Example 1 were set, so as to treat TM3 cells, and an MTT method was used to determine an optimal action concentration of the oyster peptide.

Figure 12:
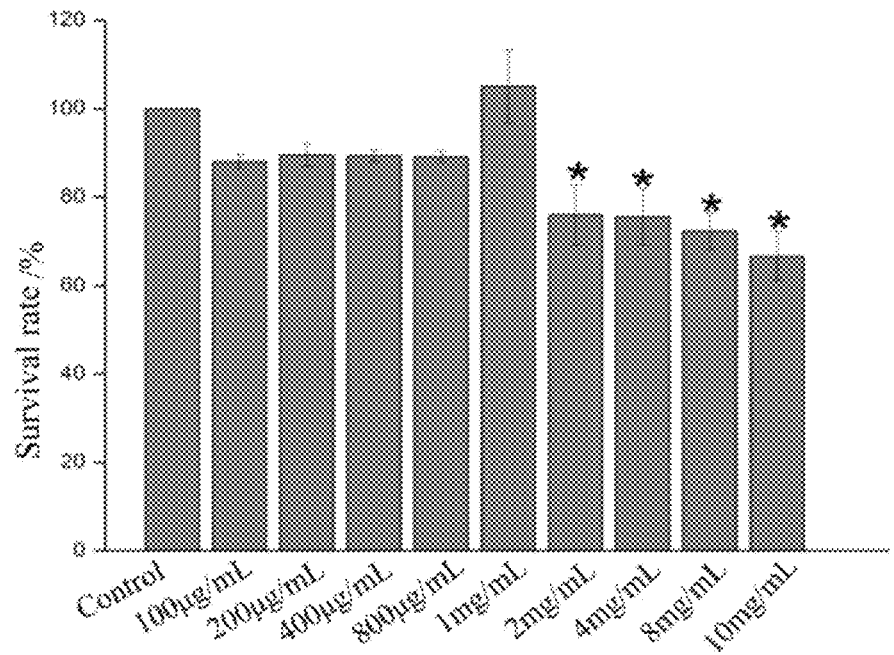
FIG. 12 is a diagram showing the relationship between a survival rate of TM3 cells and different mass concentrations of the oyster peptide in Example 1 of the present disclosure.

FIG. 12 is a diagram showing the relationship between a survival rate of TM3 cells and different mass concentrations of the oyster peptide in Example 1 of the present disclosure. As shown in FIG. 12, compared with the control group without the oyster peptide, the oyster peptide at the concentration of 100 μg/mL-1 mg/mL had no significant effect on the survival rate of TM3 cells ($P>0.05$); and the oyster peptide at the concentration in a range of 2 mg/mL-10 mg/mL had an inhibitory effect on TM3 cell activity and was concentration-dependent, which showed that the oyster peptide had a toxic effect on cells when its concentration was higher.

In order to ensure the normal growth of the cells in subsequent experiments, the loading concentration of a sample should be below a non-toxic concentration. Therefore, in the present disclosure, the loading concentration of the oyster peptide in Example 1 was set to be 100 μg/mL, 400 μg/mL, and 1 mg/mL.

b. The oyster peptides of Examples 1-3 and Comparative Examples 1-4 were prepared into culture solutions with a concentration of 400 μg/mL, respectively; and, the effects of the oyster peptides of Examples 1, 2 and 3 and Comparative Examples 1, 2, 3 and 4 on the survival rate of TM3 cells were detected by the MTT method.

Figure 13:
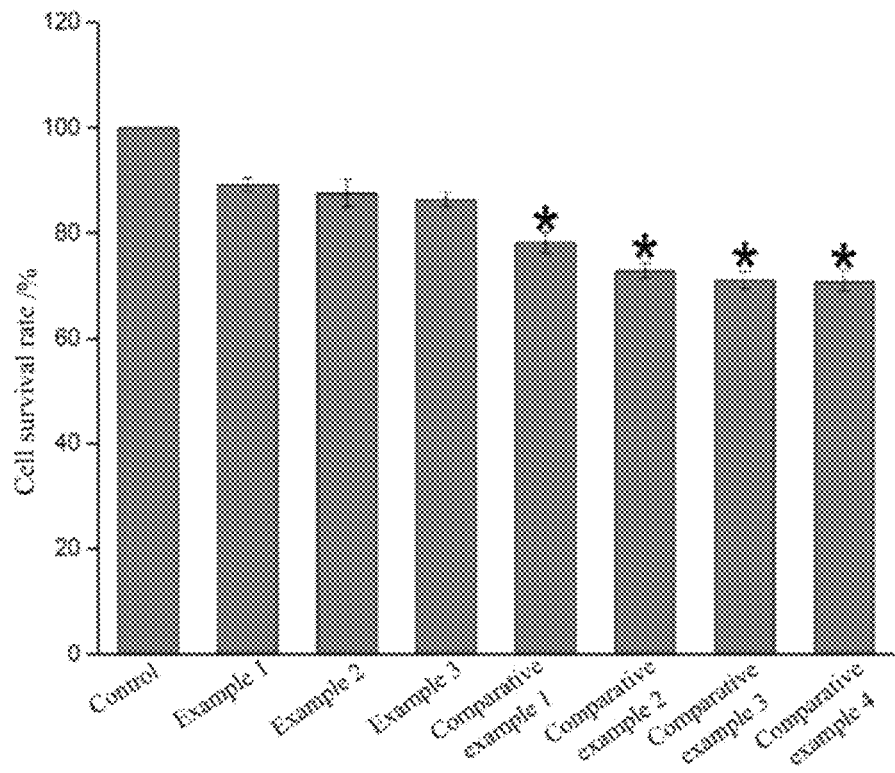
FIG. 13 is a diagram showing the relationship between each experimental group and a survival rate of TM3 cells.

FIG. 13 is a diagram showing the relationship between each test group and the survival rate of TM3 cells. As shown in FIG. 13, compared with the oyster peptides of Comparative Examples 1-4, the oyster peptides of Examples 1-3 enabled TM3 cells to have a higher survival rate.

Test Example 2

In this test example, the oyster peptide culture solution of Example 1 at a different concentration and the oyster peptide culture solutions of Examples 1-3 and Comparative Examples 1-4 at the same concentration were used to treat TM3 cells for 24 h, and then supernatant culture of cells were collected, and the contents of testosterone secreted by the cells were measured by an ELISA method.

a. The oyster peptide of Example 1 was prepared into culture solutions with different concentrations, and the effect of the oyster peptides with different concentrations in Example 1 on the content of testosterone secreted by TM3 cells was detected by the ELISA method.

Figure 14:
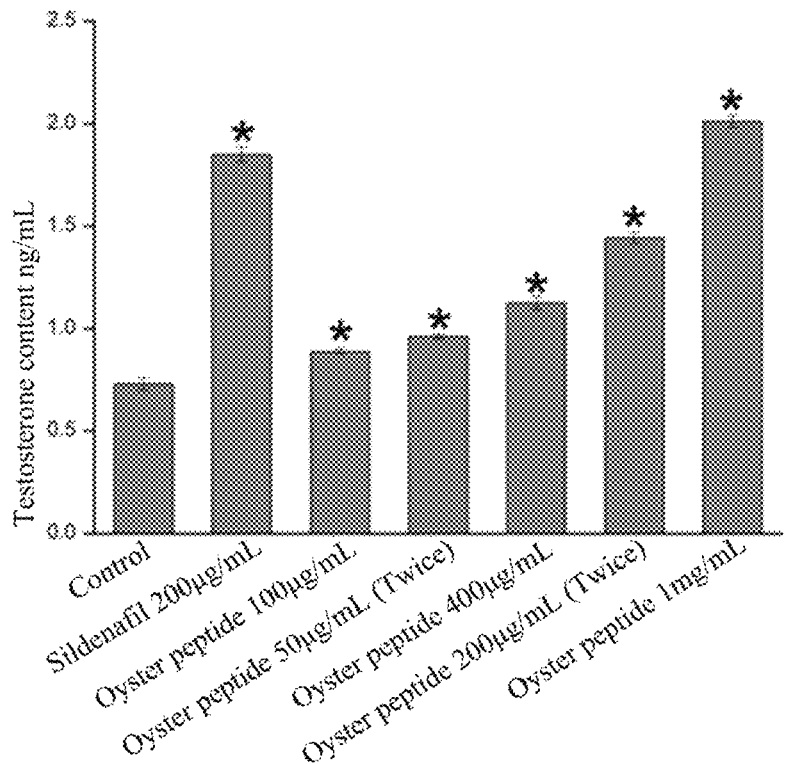
FIG. 14 is a diagram showing the relationship between a testosterone content in TM3 cells and different mass concentrations of the oyster peptide in Example 1 of the present disclosure.

FIG. 14 is a diagram showing the relationship between testosterone content in TM3 cells and different mass concentrations of the oyster peptide in Example 1 of the present disclosure. As shown in FIG. 14, compared with the control group without any oyster peptide, the oyster peptides at different concentrations significantly increased the secretion amount of testosterone in TM3 cells ($P<0.05$), and they were concentration-dependent. When the concentration of oyster peptide was 1 mg/mL, its promotion effect on secretion of testosterone in TM3 cells was higher than that of positive control sildenafil (200 μg/mL), indicating that the oyster peptide did promote the secretion of testosterone in TM3 cells.

Under the circumstance that the total amount of samples was fixed, in order to investigate the effect of different times for loading samples on cells, the concentrations of 100 μg/mL and 400 μg/mL were each divided into two doses for loading (twice in 24 h, once every 12 h), that is, 100 μg/mL was divided into two, with 50 μg/mL each time; 400 μg/mL was divided into two, with 200 μg/mL each time. It can be seen from FIG. 14 that adding the same amount of oyster peptide twice can promote the secretion of testosterone in TM3 cells better.

b. The oyster peptides of Examples 1-3 and Comparative Examples 1-4 were each prepared into a culture solution with a concentration of 400 μg/mL, and the effect of the oyster peptides of Examples 1, 2 and 3 and Comparative Examples 1, 2, 3 and 4 on the content of testosterone secreted by TM3 cells was detected by the ELISA method.

Figure 15:
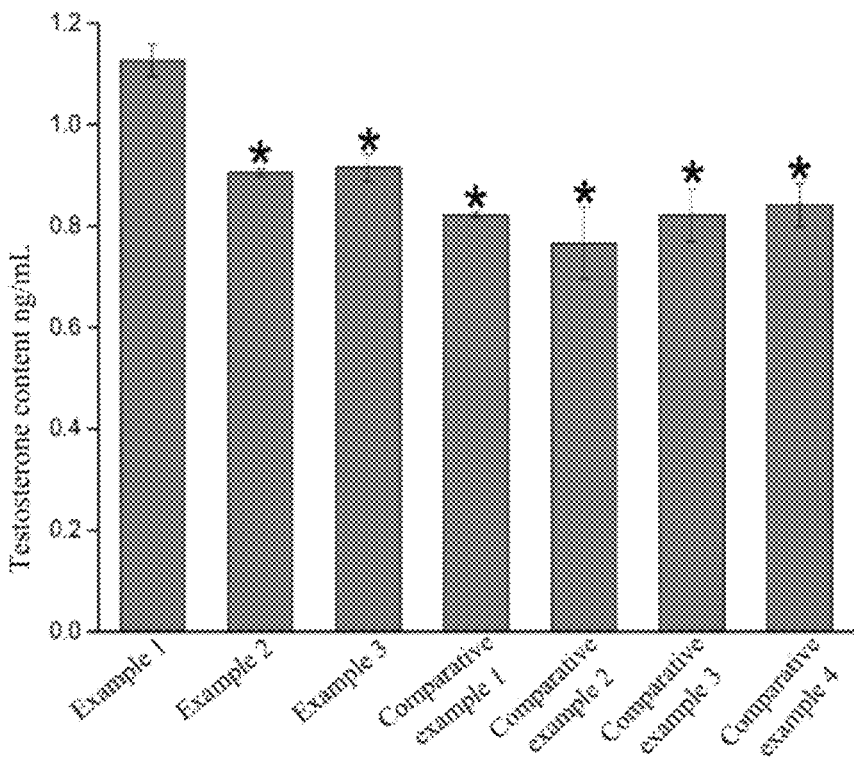
FIG. 15 is a diagram showing the relationship between each experimental group and a content of testosterone secreted by TM3 cells.

FIG. 15 is a diagram showing the relationship between each test group and the content of testosterone secreted by TM3 cells. As shown in FIG. 15, compared with the oyster peptides of Comparative Examples 1-4, the oyster peptides of Examples 1-3 can significantly promote the secretion of testosterone by TM3 cells, and Example 1 had the strongest effect on promoting the production of testosterone by TM3 cells.

Test Example 3

Figure 16:
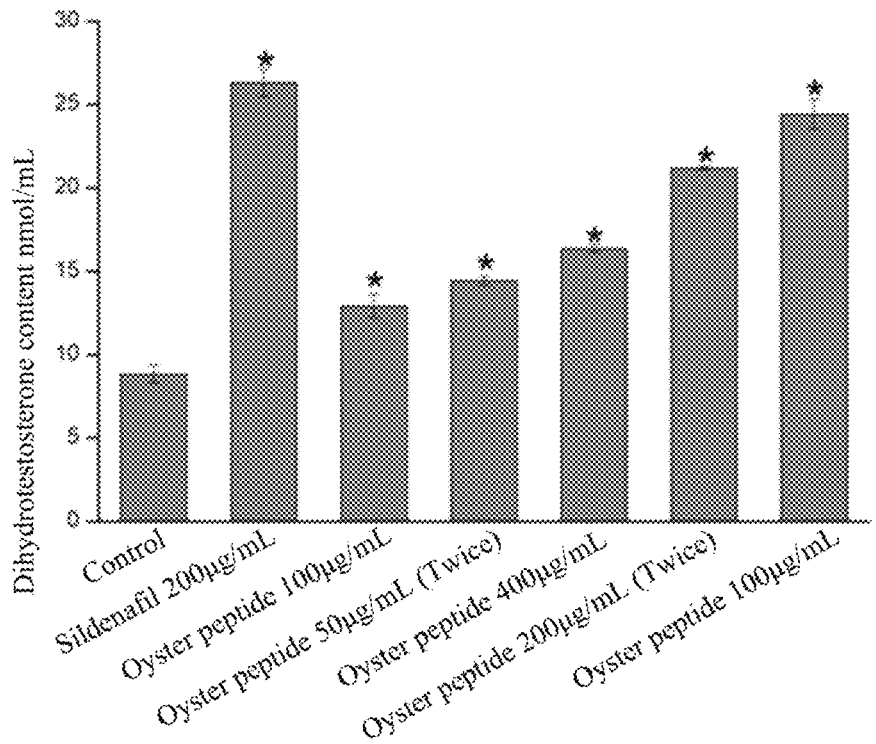
FIG. 16 is a diagram showing the relationship between a dihydrotestosterone content in TM3 cells and different mass concentrations of the oyster peptide in Example 1 of the present disclosure.

Dihydrotestosterone is a steroid hormone secreted by testes and a main male hormone in the human body, is related to the development of male secondary sexual characteristics and plays an important role in maintaining normal sexual desire. In this test example, the oyster peptide culture solutions of Example 1 at different concentrations and the oyster peptide culture solutions of Examples 1-3 and Comparative Examples 1-4 at the same concentration were used to treat TM3 cells for 24 h, and then the supernatants of cells were collected, and the contents of dihydrotestosterone secreted by the cells were measured by the ELISA method.

a. The oyster peptide of Example 1 was prepared into culture solutions at different concentrations, and the effect of different concentrations of oyster peptides in Example 1 on the content of dihydrotestosterone secreted by TM3 cells was detected by the ELISA method. FIG. 16 is a diagram showing the relationship between dihydrotestosterone content in TM3 cells and different mass concentrations of the oyster peptide in Example 1 of the present disclosure. As shown in FIG. 16, compared with the control group without any culture solution, the dihydrotestosterone content of TM3 cells in the control group was significantly lower than that of TM3 cells treated with the oyster peptide, indicating that the oyster peptide had the effect of promoting and improving dihydrotestosterone secretion by testicular interstitial cells, and it was concentration-dependent. The positive control sildenafil (200 μg/mL) also had the effect of significantly promoting the production of testosterone by TM3 cells; when the concentration of oyster peptide was 1 mg/mL, its promotion effect on the cells was similar to that of the positive control sildenafil.

Under the circumstance that the total amount of samples was fixed, in order to investigate the effect of different loading times on cells, the concentrations of 100 μg/mL and 400 μg/mL were each divided into two doses for loading (twice in 24 h, once every 12 h), that is, 100 μg/mL was divided into two, with 50 μg/mL each time; 400 μg/mL was divided into two, with 200 μg/mL each time. It can be seen from FIG. 16 that adding the same amount of oyster peptide twice can promote the secretion of dihydrotestosterone in TM3 cells better.

b. The oyster peptides of Examples 1-3 and Comparative Examples 1-4 were each prepared into a culture solution with a concentration of 400 μg/mL, and the effect of the oyster peptides of Examples 1, 2 and 3 and Comparative Examples 1, 2, 3 and 4 on the content of dihydrotestosterone secreted by TM3 cells was detected by the ELISA method.

Figure 17:
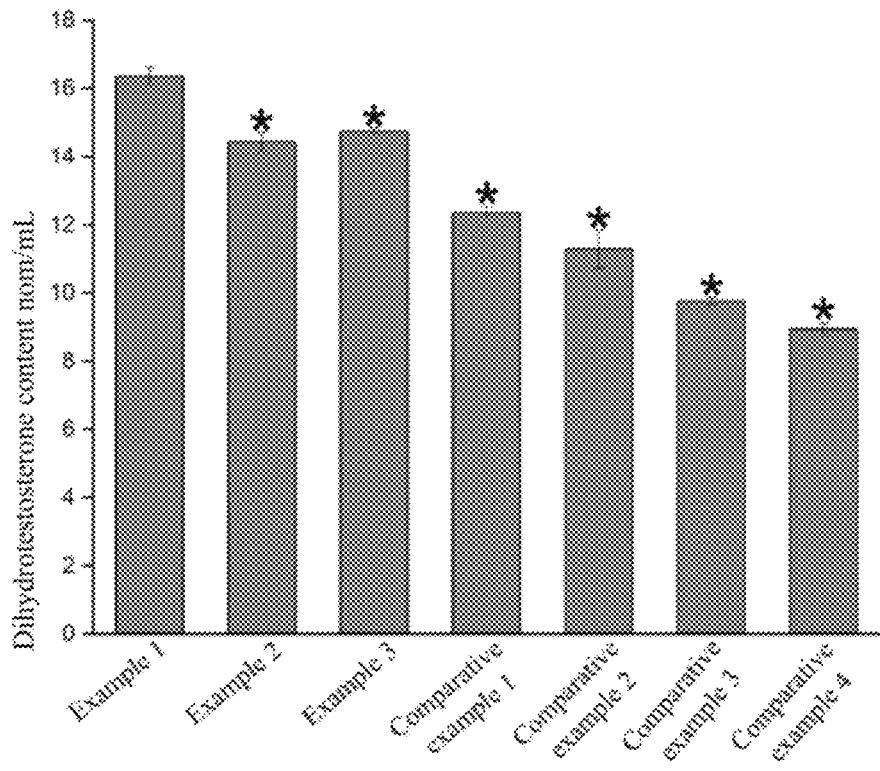
FIG. 17 is a diagram showing the relationship between each experimental group and a content of dihydrotestosterone secreted by TM3 cells.

FIG. 17 is a diagram showing the relationship between each test group and the content of dihydrotestosterone secreted by TM3 cells. As shown in FIG. 17, compared with the oyster peptides of Comparative Examples 1-4, the oyster peptides of Examples 1-3 can significantly promote the secretion of dihydrotestosterone by TM3 cells, and the oyster peptide of Example 1 had the strongest effect on promoting the production of dihydrotestosterone by TM3 cells.

Test Example 4

Figure 18:
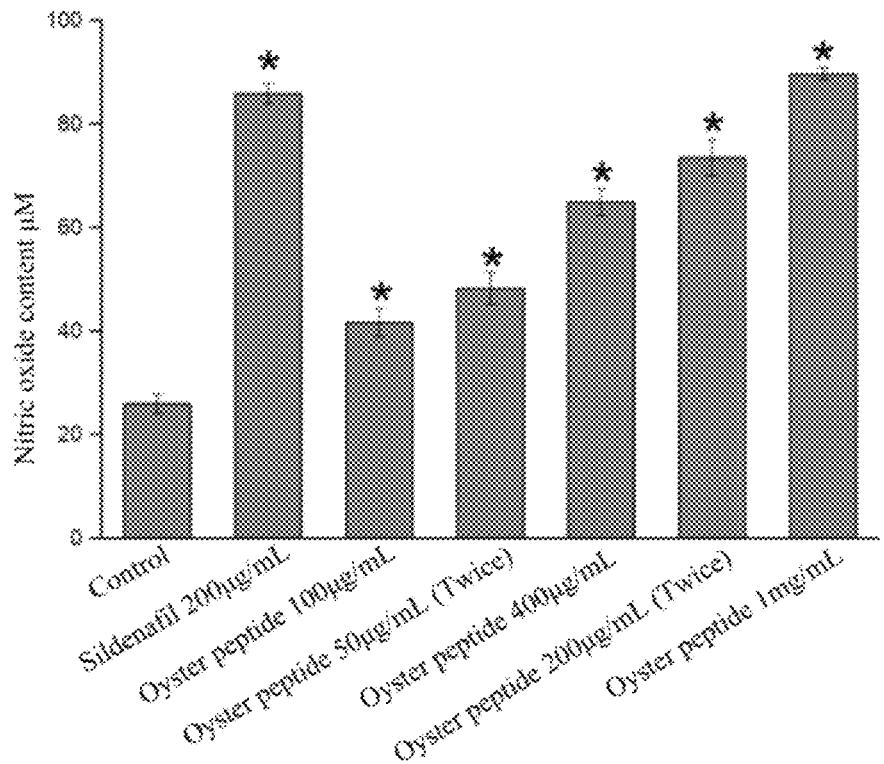
FIG. 18 is a diagram showing the relationship between NO content in TM3 cells and different mass concentrations of the oyster peptide in Example 1 of the present disclosure.

NO is a small fat-soluble molecule with unstable chemical properties and is produced by a catalyzed reaction of nitric oxide synthase in a body, and it can cause the expansion of blood vessels in the body. Therefore, it is an important messenger for relaxation of cavernous body of a penis, and has a decisive effect on the process of inducing and maintaining penile erection. In this test example, the culture solutions of oyster peptide of Example 1 at different concentrations and the culture solutions of oyster peptide of Examples 1-3 and Comparative Examples 1-4 at the same concentration were used to treat TM3 cells for 24 h and then centrifuged, and supernatants were collected and mixed uniformly. The effect of the oyster peptide on the NO content in TM3 cells was detected according to the instructions of NO determination kit.

a. The oyster peptide of Example 1 was prepared into culture solutions at different concentrations, and the effect of different concentrations of oyster peptides in Example 1 on the NO content in TM3 cells was detected by NO determination kit. FIG. 18 is a diagram showing the relationship between the NO content in TM3 cells and different mass concentrations of the oyster peptide in Example 1 of the present disclosure. As shown in FIG. 18, compared with TM3 cells in the control group without any culture solution, the NO content in TM3 cells in the positive control sildenafil (200 μg/mL) and the oyster peptides in test groups both increased significantly ($p<0.05$).

Under the circumstance that the total amount of samples was fixed, in order to investigate the effect of different loading times on cells, the concentrations of 100 μg/mL and 400 μg/mL were each divided into two doses for loading (twice in 24 h, once every 12 h), that is, 100 μg/mL was divided into two, with 50 μg/mL each time; 400 μg/mL was divided into two, with 200 μg/mL each time. It can be seen from FIG. 18 that the NO content in the treated cells increased more obviously after the oyster peptide was loaded in two doses to treat TM3 cells.

b. The oyster peptides of Examples 1-3 and Comparative Examples 1-4 were each prepared into a culture solution with a concentration of 400 μg/mL, and the effect of the oyster peptides of Examples 1, 2 and 3 and Comparative Examples 1, 2, 3 and 4 on the content of NO in TM3 cells was detected by NO determination kit.

Figure 19:
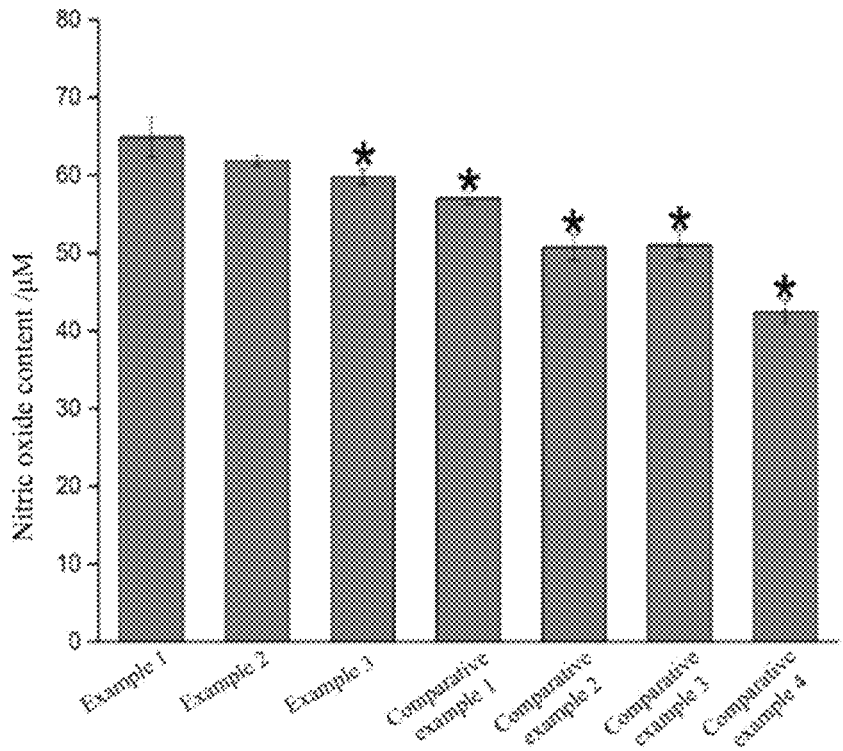
FIG. 19 is a diagram showing the relationship between each experimental group and a NO content in TM3 cells.

FIG. 19 is a diagram showing the relationship between each test group and the NO content in TM3 cells. As shown in FIG. 19, compared with the oyster peptides of Comparative Examples 1-4, the oyster peptides of Examples 1-3 can significantly improve the NO content in TM3 cells, and the oyster peptide of Example 1 had the strongest effect on improving the NO content in TM3 cells.

Test Example 5

Figure 20:
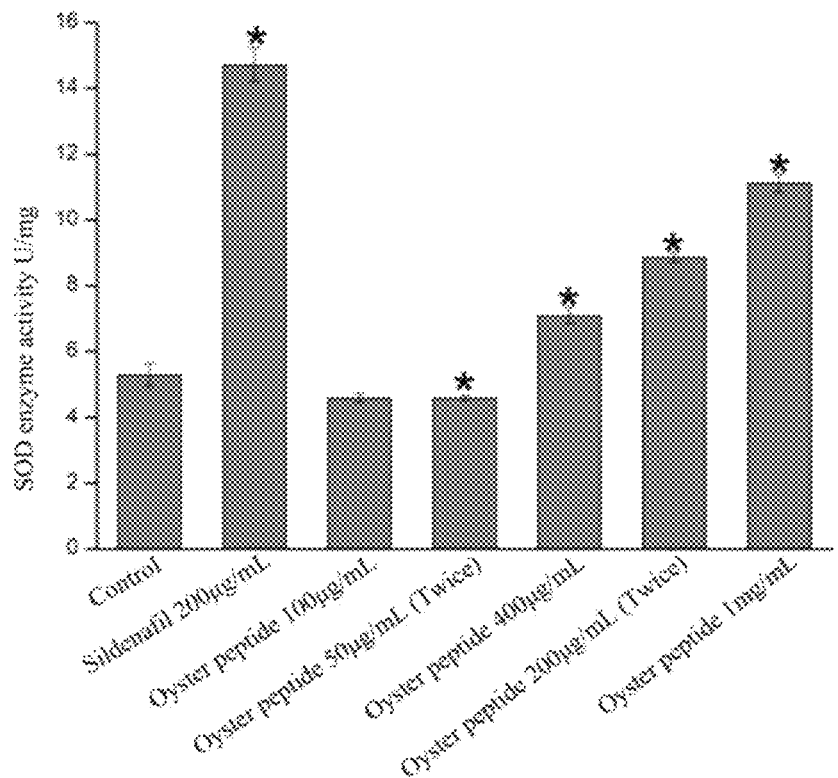
FIG. 20 is a diagram showing the relationship between SOD activity in TM3 cells and different mass concentrations of the oyster peptide in Example 1 of the present disclosure.

Superoxide dismutase (SOD) is an active substance in organisms, which can eliminate harmful substances produced by the organisms in a metabolism process. SOD can catalyze the conversion of superoxide free radicals into hydrogen peroxide and molecular oxygen, and play a key role in resisting cell damages caused by oxygen free radicals. In order to evaluate oxidation environment of TM3 cells. In this test example, the culture solutions of oyster peptide of Example 1 at different concentrations and the culture solutions of oyster peptide of Examples 1-3 and Comparative Examples 1-4 at the same concentration were used to treat TM3 cells for 24 h and then centrifuged, and supernatants were collected and mixed uniformly. SOD activity in cells was detected according to the instructions of SOD determination kit.

a. The oyster peptide of Example 1 was prepared into culture solutions at different concentrations, and the effect of different concentrations of the oyster peptide in Example 1 on the SOD enzyme activity in TM3 cells was detected by SOD enzyme determination kit. FIG. 20 is a diagram showing the relationship between SOD activity in TM3 cells and different mass concentrations of the oyster peptide in Example 1 of the present disclosure. As shown in FIG. 20, the SOD enzyme activity in cells of the oyster peptide groups increased significantly, compared with the control group without any culture solution ($p<0.05$), and the effect of the high-dose group (1 mg/mL) was significantly better than that of the low-dose group (100 μg/mL), showing a certain dose dependence. After TM3 cells were treated with the oyster peptide, the enzyme activity of SOD may be significantly enhanced, which enabled the oxidation environment within the cells to facilitate the production of testosterone and other male hormones.

Under the circumstance that the total amount of samples was fixed, in order to investigate the effect of different loading times on cells, the concentrations of 100 μg/mL and 400 μg/mL were each divided into two doses for loading (twice in 24 h, once every 12 h), that is, 100 μg/mL was divided into two, with 50 μg/mL each time; 400 μg/mL was divided into two, with 200 μg/mL each time. It can be seen from FIG. 20 that the SOD activity of the treated cells increased more obviously after the oyster peptide was loaded in two doses to treat TM3 cells.

b. The oyster peptides of Examples 1-3 and Comparative Examples 1-4 were each prepared into a culture solution with a concentration of 400 μg/mL, and the effect of the oyster peptides of Examples 1, 2 and 3 and Comparative Examples 1, 2, 3 and 4 on the SOD activity in TM3 cells was detected by a SOD determination kit.

Figure 21:
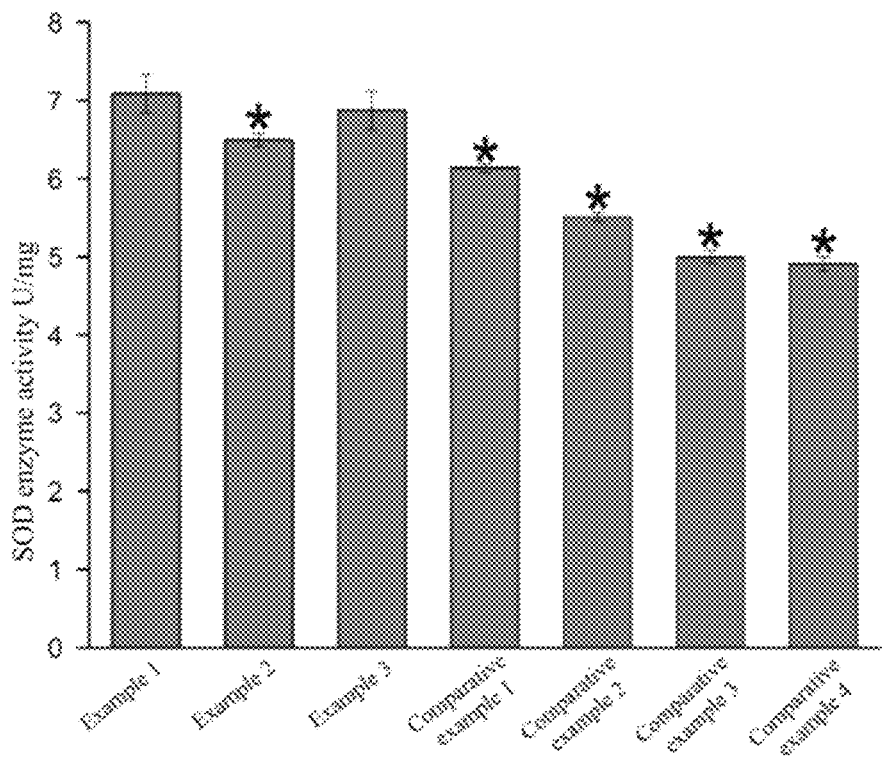
FIG. 21 is a diagram showing the relationship between each experimental group and SOD activity in TM3 cells.

FIG. 21 is a diagram showing the relationship between each test group and SOD activity in TM3 cells. As shown in FIG. 21, compared with the oyster peptides of Comparative Examples 1-4, the oyster peptides of Examples 1-3 can significantly improve the SOD activity in TM3 cells, and the oyster peptide of Example 1 had the strongest effect on improving the SOD activity in TM3 cells.

Test Example 6

Figure 22:
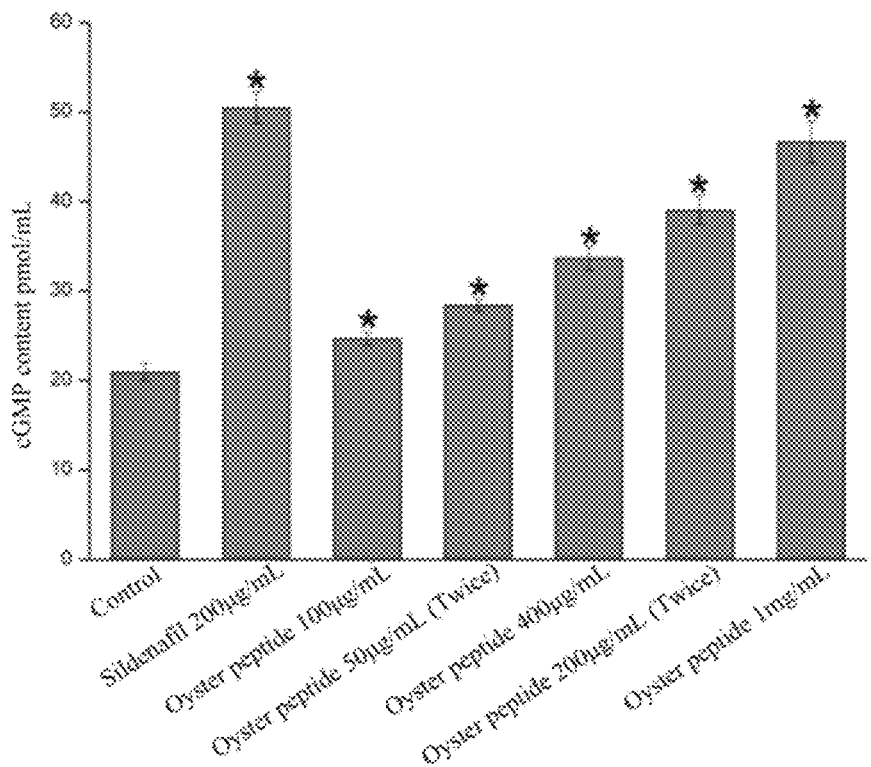
FIG. 22 is a diagram showing the relationship between a cGMP content in TM3 cells and different mass concentrations of the oyster peptide in Example 1 of the present disclosure.

In this test example, the culture solutions of oyster peptide of Example 1 at different concentrations and the culture solutions of oyster peptide of Examples 1-3 and Comparative Examples 1-4 at the same concentration were used to treat TM3 cells for 24 h, and then centrifuged, and supernatants were collected and mixed uniformly. cGMP content in cells was detected according to the instructions of cGMP determination kit.

a. The oyster peptide of Example 1 was prepared into culture solutions at different concentrations, and the effect of different concentrations of the oyster peptide in Example 1 on the cGMP content in TM3 cells was detected by cGMP determination kit. FIG. 22 is a diagram showing the relationship between the cGMP content in TM3 cells and different mass concentrations of the oyster peptide in Example 1 of the present disclosure. As shown in FIG. 22, compared with the control group without any culture solution, the oyster peptide can significantly increase the content of cGMP in TM3 cells, and its effect became stronger with the increase of the concentration of the oyster peptide.

Under the circumstance that the total amount of samples was fixed, in order to investigate the effect of different loading times on cells, the concentrations of 100 μg/mL and 400 μg/mL were each divided into two doses for loading (twice in 24 h, once every 12 h), that is, 100 μg/mL was divided into two doses, with 50 μg/mL each time; 400 μg/mL was divided into two doses, with 200 μg/mL each time. It can be seen from FIG. 22 that, similarly, we found that adding the same amount of oyster peptide twice can promote the secretion of cGMP by TM3 cells better.

b. The oyster peptides of Examples 1-3 and Comparative Examples 1-4 were each prepared into a culture solution with a concentration of 400 μg/mL, and the effect of the oyster peptides of Examples 1, 2 and 3 and Comparative Examples 1, 2, 3 and, 4 on the cGMP content in TM3 cells was detected by a cGMP determination kit.

Figure 23:
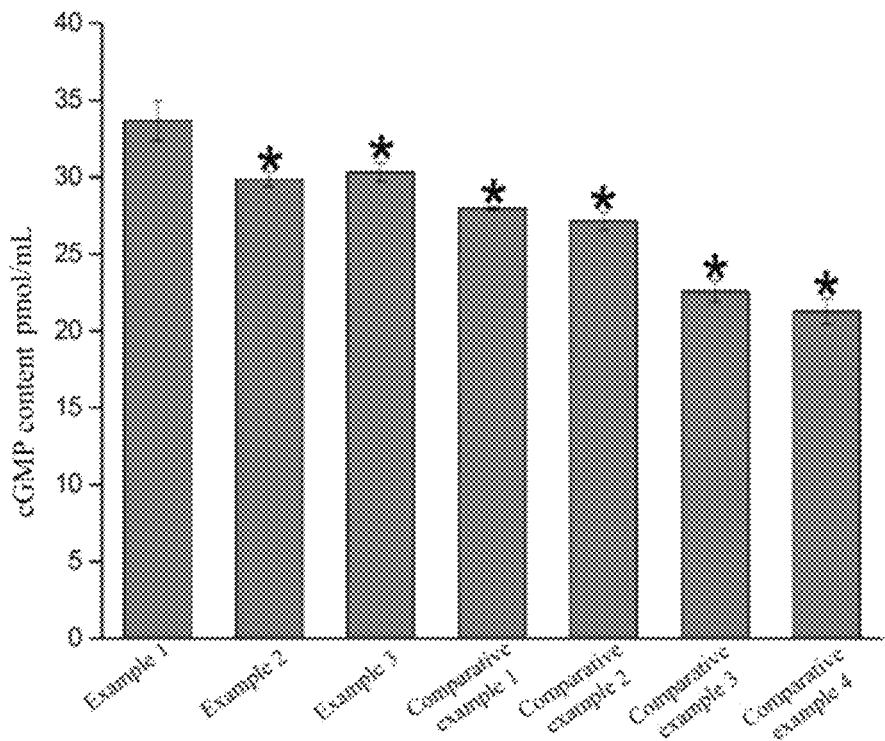
FIG. 23 is a diagram showing the relationship between each experimental group and a cGMP content in TM3 cells.

FIG. 23 is a diagram showing the relationship between each test group and the cGMP content in TM3 cells. As shown in FIG. 23, compared with the oyster peptides of Comparative Examples 1-4, the oyster peptides of Examples 1-3 can significantly promote the increase of cGMP content in TM3 cells, and the oyster peptide of Example 1 had the strongest effect on promoting the secretion of cGMP by TM3 cells.

In FIGS. 12-23, "*" denotes the comparison with the blank group, P<0.05.

Finally, it should be noted that the above embodiments are only intended for illustrating technical solutions of the present disclosure other than limitation. Although the present disclosure has been described in detail with reference to the foregoing embodiments, those skilled in the art shall understand that modifications can still be made on the technical solutions described in the foregoing embodiments, or equivalent substitutions can be made on some or all of the technical features therein; and, these modifications or substitutions will not make the essence of the corresponding technical solutions depart from the scope of the technical solutions in the embodiments of the present disclosure.

What is claimed is:

1. An oyster oligopeptide composition, wherein the oyster oligopeptide composition at least comprises peptide segments RI, IR and VR in its composition; based on a mass of the oyster oligopeptide composition, a content of the RI is ≥3.60 mg/100 g, a content of the IR is ≥7.60 mg/100 g, and a content of the VR is ≥6.50 mg/100 g;

wherein the oyster oligopeptide composition is prepared as follows:
1) adding water to an oyster meat raw material to obtain a mixed material liquid, adding concentrated hydrochloric acid to the mixed material liquid and stirring, and collecting a precipitate after solid-liquid separation;
2) adding water to the precipitate to obtain a slurry, adding alkali to perform a protein denaturation treatment at 85-90° C., so as to obtain a denatured solution of oyster protein;
3) adding a neutral protease and a papain to the denatured solution of oyster protein, and performing enzymolysis treatment for 3-6 h, so as to obtain an enzymolysis solution after the neutral protease and the papain are inactivated;
4) centrifuging the enzymolysis solution to obtain a centrifugal supernatant, and then performing treatments of filtration and column chromatography on the centrifugal supernatant in sequence, so as to obtain the oyster oligopeptide composition.

2. The oyster oligopeptide composition according to claim 1, wherein a mass content of peptides with a molecular weight less than 1000 u in the oyster oligopeptide composition is ≥90%.

3. The oyster oligopeptide composition according to claim 1, wherein in step 1), a mass-to-volume ratio of the oyster meat raw material to the water is 1:(5-8), and an acid treatment is carried out by adding 3-5 mL of the concentrated hydrochloric acid per kilogram of the oyster meat raw material.

4. The oyster oligopeptide composition according to claim 1, wherein solid sodium hydroxide is used for the protein denaturation treatment, and after addition of solid sodium hydroxide to the slurry in a mass ratio of 0.8-1.0 g of the solid sodium hydroxide per kilogram of the oyster meat raw material, a temperature is increased to 85-90° C. and kept for 60-120 min under stirring.

5. The oyster oligopeptide composition according to claim 1, wherein based on a mass of the oyster meat raw material, an amount of the neutral protease is 0.8-1.6 AU/1000 g, and an amount of the papain is 100000-300000 U/1000 g.

6. The oyster oligopeptide composition according to claim 1, wherein the filtration comprises: filtering the centrifugal supernatant by a ceramic membrane with a pore size of 50-200 nm, and collecting a filtrate.

7. The oyster oligopeptide composition according to claim 1, wherein the column chromatography treatment comprises: performing a purification treatment on a filtrate obtained by the filtration by a cation chromatography column and a hydrophobic chromatography column in sequence;

wherein a packing for the cation chromatography column has a particle size of 0.315-1.25 mm; and a packing for the hydrophobic chromatography column has a particle size of 45-165 μm.

* * * * *